United States Patent
Mitchell et al.

(10) Patent No.: US 10,293,054 B2
(45) Date of Patent: May 21, 2019

(54) LIPOFULLERENE-SACCHARIDE CONJUGATES AND THEIR USE AS ANTIMETASTATIC AGENTS FOR THE INHIBITION OF MAMMALIAN NEOPLASMS

(71) Applicant: LivePet, LLC, Austin, TX (US)

(72) Inventors: Ian Mitchell, Bartlesville, OK (US); Ayyappan Subbiah, Bartlesville, OK (US); Daniel David Bensimon, Austin, TX (US)

(73) Assignee: LivePet, LLC, Austin, TX (US)

( * ) Notice: Subject to any disclaimer, the term of this patent is extended or adjusted under 35 U.S.C. 154(b) by 0 days.

(21) Appl. No.: 15/903,868

(22) Filed: Feb. 23, 2018

(65) Prior Publication Data

US 2018/0256728 A1    Sep. 13, 2018

Related U.S. Application Data

(60) Provisional application No. 62/462,870, filed on Feb. 23, 2017.

(51) Int. Cl.
| | |
|---|---|
| *A61K 33/44* | (2006.01) |
| *A61K 47/54* | (2017.01) |
| *A61P 35/04* | (2006.01) |
| *A61K 31/015* | (2006.01) |
| *A61K 31/20* | (2006.01) |
| *C01B 32/156* | (2017.01) |
| *C01B 32/152* | (2017.01) |
| *A61K 47/69* | (2017.01) |

(52) U.S. Cl.
CPC .......... *A61K 47/549* (2017.08); *A61K 31/015* (2013.01); *A61K 31/20* (2013.01); *A61K 33/44* (2013.01); *A61K 47/555* (2017.08); *A61K 47/6949* (2017.08); *A61P 35/04* (2018.01); *C01B 32/152* (2017.08); *C01B 32/156* (2017.08)

(58) Field of Classification Search
None
See application file for complete search history.

(56) References Cited

U.S. PATENT DOCUMENTS

| | | | |
|---|---|---|---|
| 7,001,888 B2 * | 2/2006 | Tidmarsh | A61K 47/549 514/23 |
| 7,070,810 B2 | 4/2006 | Hirsch et al. | |
| 9,308,243 B2 | 4/2016 | Mitchell et al. | |
| 2008/0206222 A1 | 8/2008 | Miwa et al. | |
| 2009/0258841 A1 | 10/2009 | Murphy et al. | |
| 2010/0040599 A1 | 2/2010 | Yudoh | |
| 2015/0258181 A1 | 9/2015 | Mitchell et al. | |

FOREIGN PATENT DOCUMENTS

WO    WO03/068185    *  8/2003    ............. A61K 9/00

OTHER PUBLICATIONS

Biller et al., "2016 AAHA Oncology Guidelines for Dogs and Cats" Journal of the American Animal Hospital Association: Jul./Aug. 2016, vol. 52, No. 4, pp. 181-204 (Year: 2016).*
Otake et al., "Effect and Mechanism of a New Photodynamic Therapy with Glycoconjugated Fullerene" Photochemistry and Photobiology vol. 86 pp. 1356-1363 (Year: 2010).*
Ishi-i et al., "Saccharide Libraries as Potential Templates for Regio- and Chiroselective Introduction of Two Functional Groups into [60]Fullerene" Journal of Organic Chemistry vol. 64 pp. 984-990 (Year: 1999).*
Agostoni et al. "Scientific Opinion on the substantiation of health claims related to L-carnosine and increase in muscle power (ID 1824), increase in endurance capacity (ID 1824), "skin" (ID 1825) and maintenance of normal cardiac function (ID 1826) pursuant to Article 13(1) of Regulation (EC) No. 1924120061", EFSA Journal 2011; 9(4):2038.
Andreichenko et al. "Effect of Fullerene C60 on ATPase Activity and Superprecipitation of Skeletal Muscle Actomyosin" ISSN 0201-8470. BioChem, 2013, m. 85, No. 2.
Andrievsky et al. "First clinical case of treatment of patient (volunteer) with rectal adenocarcinoma by hydrated C60 fullerenes: natural course of the disease or non-specific anticancer activity?".
Baati et al. "The prolongation of the lifespan of rats by repeated oral administration of [60] fullerene" Biomaterials xxx (2012)1-11.
Bakry et al. "Medicinal applications of fullerenes" International Journal of Nanomedicine 2007:2(4) 639-649.
Boldyrev et al. "Carnosine, the Protective, Anti-aging Peptide" Bioscience Reports, vol. 19, No. 6, 1999.
Chen et al. "Applications of Functionalized Fullerenes in Tumor Theranostics" Theranostics 2012, 2(3):238-250.
Chistyakov et al. "Feasibility of the C60 Fullerene Antioxidant Properties: Study with Density Functional Theory Computer Modeling" Proceedings of the 2013 International Conference on Biology, Medical Physics, Medical Chemistry, Biochemistry and Biomedical Engineering.
Culbertson et al. "Effects of Beta-Alanine on Muscle Carnosine and Exercise Performance: A Review of the Current Literature" Nutrients 2010, 2, 75-98.

(Continued)

*Primary Examiner* — Eric Olson
(74) *Attorney, Agent, or Firm* — Meyertons, Hood, Kivlin, Kowert & Goetzel, P.C.

(57) ABSTRACT

In some embodiments, a lipofullerene-saccharide compound and a method of inhibiting and/or ameliorating metastasis of neoplastic cells using said compound is disclosed herein. The lipofullerene-saccharide compound may be used in therapeutically effective doses to inhibit the metastasis of neoplasms in mammals. In some embodiments, the method may include administering to a subject an effective amount of a pharmaceutically acceptable formulation including a lipofullerene-saccharide compound. In some embodiments, the lipofullerene-saccharide compound may be formed by reacting (e.g., coupling) a lipid and a saccharide with a fullerene. In some embodiments, neoplastic cells may include pancreatic cancer cells, prostate cancer cells, lung cancer cells, breast cancer cells, colon cancer cells, and/or brain cancer cells. A significant anti-metastatic effect has been observed on a metastatic nude-mouse model of human pancreatic cancer BxPC-3 cell lines constructed orthotopically as a result of therapeutic treatment with the lipofullerene-saccharide conjugate.

16 Claims, 16 Drawing Sheets

(56) References Cited

OTHER PUBLICATIONS

Grebowski et al. "Fullerenols as a New Therapeutic Approach in Nanomedicine" BioMed Research International vol. 2013, Article ID 751913, 9 pages.
Hipkiss et al. "Carnosine: can understanding its actions on energy metabolism and protein homeostasis inform its therapeutic potential?" Chemistry Central Journal 2013, 7:38.
Huczko et al. "Fullerenes: Experimental Evidence for a Null Risk of Skin Irritation and Allergy" Fullerene Science and Technology, 7(5), 935-939 (1999).
Johnston et al. "The Biological Mechanisms and Physicochemical Characteristics Responsible for Driving Fullerene Toxicity" Toxicological Sciences 114(2), 162-182 (2010).
Monti et al. "C60 Carboxyfullerene Exerts a Protective Activity against Oxidative Stress-Induced Apoptosis in Human Peripheral Blood Mononuclear Cells" Biochemical and Biophysical Research Communications 277,711-717 (2000).
Murugesan et al. "Carbon inhibits vascular endothelial growth factor- and fibroblast growth factor-promoted angiogenesis" FEBS Letters 581 (2007) 1157-1160.
Prylutska et al. "Using water-soluble C60 fullerenes in anticancer therapy" Cancer Nano (2011) 2:105-110.
Rajinikanth et al. "Investigations on the Potential of Ser-ratiopeptidase—a Proteolytic Enzyme, on Acetic Acid Induced Ulcerative Colitis in Mice" Int J Pharm Pharm Sci, vol. 6, Issue 5, 525-531.
Sellman et al. "Serrapeptase An Amazing Gift from the Silk Worm" 2003.
Tsao et al. "In vitro action of carboxyfullerene" Journal of Antimicrobial Chemotherapy (2002) 49, 641-649.
Velasco et al. "Oxidative stability of virgin olive oil" Eur. J. Lipid Sci. Technol. 104 (2002) 661-676.
Yin et al. "The scavenging of reactive oxygen species and the potential for cell protection by functionalized fullerene materials" Biomaterials 30 (2009) 611-621.
Zhou "Liposome Formulation of Fullerene-Based Molecular Diagnostic and Therapeutic Agents" Pharmaceutics 2013, 5, 525-541.

International Wellness Directory, http://www.mnwelldir.org/docs/terrain/chronic_inflammation.htm "Chronic Inflammation" 2007.
Non Final Office Action for U.S. Appl. No. 14/656,304 dated May 12, 2015.
Final Office Action for U.S. Appl. No. 14/656,304 dated Sep. 8, 2015.
Notice of Allowance for U.S. Appl. No. 14/656,304 dated Dec. 8, 2015.
Kozina et al. "Antioxidant Properties of Geroprotective Peptides of the Pineal Gland" (Arch. Gerontol. Geriatr. S1 :213-216 (2007).
Drafi et al. "Carnosine inhibits degradation of hyaluronan induced by free radical processes in vitro and improves the redox imbalance in adjuvant arthritis in vivo" (Neuroendocrin. Let., 31(2):96-100 (2010).
McPhee et al. "Anti-cyclooxygenase effects of lipid extracts from the New Zealand green-lipped mussel, *Perna Canaliculus*" (Comp. Biochem. Phys., Part B, 146:346-356 (2007).
"New Cellular Target May Put the Brakes on Cancer's Ability to Spread" http://releases.jhu.edu/2017/05/26/new-cellular-target-may-put-the-brakes-on-cancers-ability-to-spread/, May 26, 2017.
Jayatilaka et al. "Synergistic IL-6 and IL-8 paracrine signalling pathway infers a strategy to inhibit tumour cell migration", Nature Communications, May 26, 2017.
Porporato et al. "A Mitochondrial Switch Promotes Tumor Metastasis", Cell Reports, vol. 8, Issue 3, p. 754-766, Aug. 7, 2014, Published online Jul. 24, 2014.
International Search Report and Written Opinion for PCT/US18/19463 dated May 4, 2018 pp. 10.
Bolskar 'Fullerenes for Drug Delivery', Encyclopedia of Nanotechnology, 2012, pp. 1267-1281; p. 1272, p. 1273, p. 1276.
Jie et al. 'Fullerene Lipids: Synthesis of C60 Fullerene Derivatives Bearing a Long-Chain Saturated or Unsaturated Triester System', Lipids, Nov. 1, 1999 (Nov. 1, 1999), vol. 34, pp. 1223-1230; Title, p. 1223, p. 1226, p. 1227.
Nierengarten et al. 'Fullerene Sugar Balls: A New Class of Biologically Active Fullerene Derivatives', Chemistry An Asian Journal, May 15, 2014 (May 15, 2014), vol. 9, pp. 1436-1444; Abstract, p. 1437, p. 1438, p. 1441.

* cited by examiner

LIPOFULLERENE-SACCHARIDE CONJUGATES AND THEIR USE AS ANTIMETASTATIC AGENTS FOR THE INHIBITION OF MAMMALIAN NEOPLASMS

PRIORITY CLAIM

This application claims priority to U.S. Provisional Patent Application No. 62/462,870 entitled "LIPOFULLERENE-SACCHARIDE CONJUGATES AND THEIR USE AS ANTIMETASTATIC AGENTS FOR THE INHIBITION OF MAMMALIAN NEOPLASMS" filed on Feb. 23, 2017, which is incorporated by reference herein.

BACKGROUND OF THE INVENTION

1. Field of the Invention

The present disclosure generally relates to a pharmaceutically acceptable formulation inhibiting and/or ameliorating metastasis of neoplasms in mammals. More particularly, the disclosure generally relates to a pharmaceutically acceptable formulation comprising a lipofullerene-saccharide conjugate for use as an antimetastatic agent to help diminish and/or negate the spread of neoplasms in mammalian systems.

2. Description of the Relevant Art

The present disclosure relates to compositions based at least in part on fullerenes. Since the discovery of fullerenes (Carbon 60 (C60)) in 1985, fullerenes have triggered interest in the scientific community based upon fullerenes' interesting properties. Fullerene has been found to comprise a number of desirable structural, physical, and chemical properties adaptable for biological uses including antioxidants, anti-inflammatory, drug delivery, and photodynamic therapy.

Because of their spherical shape, structural similarity and their tilde one nanometer size, fullerenes are often denoted as buckyballs or carbon nanomaterials. C60 has a uniquely delocalized $\pi$ electron cloud across the cage surface with each carbon atom contributing one $\pi$ electron, rendering fullerene with very high electron affinity. The absence of any reactive site on the cage surface except the carbon-carbon double bonds often makes the cage inert under physiological conditions. From the chemistry perspective, fullerenes are super-conjugated, electron deficient poly-olefins. From the biology perspective, fullerenes are super-powerful antioxidants capable of scavenging and detoxifying reactive oxygen species (ROS) and reactive nitrogen species (RNS).

Various functionalized fullerenes were synthesized through chemical or supra-molecular approaches, usually a chemical modification on the surface of the sphere, to achieve promising results. Most likely due to its unique chemical structure, C60 possesses interesting photo-physical properties and generates reactive oxygen species by exposure to visible light, making it a potentially strong agent for photodynamic therapy in biological systems. Fullerenes can efficiently generate reactive oxygen species when exposed to visible light, which means it may be an effective cytotoxic agent.

The anatomical characteristics of tumors, such as hyperpermeable vasculature and an immature lymphatic system, resulting in large-sized substances being able to accumulate and remain longer in tumor tissues than in normal tissues. When C60 was conjugated with polyethylene glycol (PEG), pullulan, etc., strong tumor suppression was shown after the conjugate was injected intravenously into tumor-bearing mice coupled with light irradiation. Fullerenes and their derivatives have been proposed as free radical scavengers, and a number of investigations have studied fullerene derivatives as potential free radical antioxidant therapeutics, neuro-protectants, anti-inflammatories and others. The photochemical properties of C60 to date have yielded potentially the most interesting biological application; it can be used in photodynamic therapy of cancer as various photo-excited C60 complexes generate reactive oxygen species which can cleave DNA and can cause apoptosis (cell death).

Aqueous suspensions were previously used to investigate the acute and sub-acute toxicities as well as the in vivo antioxidant properties of C60. When taken in-vivo, C60 complexes resulted in varying degree of toxicity. But, such suspensions are not appropriate for determining toxicity at reiterated doses, because fullerene is active only in soluble form and because the extremely slow dissolution of C60 in biological media prevents controlling accurately the active fraction.

It was reported that lipolizing C60 using long chain triglycerides circumvented the C60 solubility issue. Their study revealed the life span enhancing properties of in vivo lipo-fullerene on Wistar rats. Also, absence of tumors in all animals in the test group was noted.

According to the American Cancer Society's most recent estimates for pancreatic cancer in the United States, about 46,420 people (23,530 men and 22,890 women) will be diagnosed with pancreatic cancer and about 39,590 people (20,170 men and 19,420 women) will die of pancreatic cancer in the year 2014. Rates of pancreatic cancer have been increasing slightly over the past decade or so. Pancreatic cancer accounts for about 3% of all cancers in the US, and accounts for about 7% of cancer deaths.

Therefore, a composition which inhibits and/or ameliorates metastasis of neoplasms in mammals would be highly desirable.

SUMMARY

In some embodiments, a lipofullerene-saccharide compound and a method of inhibiting and/or ameliorating metastasis of neoplastic cells using said compound is disclosed herein. In some embodiments, the lipofullerene-saccharide conjugate may be formed by reacting (e.g., coupling) a lipid and a saccharide with a fullerene. In some embodiments, the lipofullerene saccharide may include a structural formula of $[C60]x[C6H12O6]y[C18H34O2]z$. x may be greater than or equal to 1, y may be greater than or equal to 1, and z may be greater than or equal to 1.

In some embodiments, the fullerene may include C60. Fullerenes may include molecules of carbon in the form of a hollow sphere, ellipsoid, tube, and many other shapes.

In some embodiments, the lipid may include a fatty acid. A lipid may refer to a substance of biological origin that is soluble in nonpolar solvents or more generally as hydrophobic or amphiphilic small molecules. Specific examples of lipids may include fats, waxes, sterols, fat-soluble vitamins (e.g., vitamins A, D, E, and K), monoglycerides, diglycerides, triglycerides, and phospholipids. In some embodiments, the lipid may include a structural formula of $C18H34O2$.

In some embodiments, the saccharide may include a sugar. A sugar may refer to a biological molecule consisting of carbon (C), hydrogen (H) and oxygen (O) atoms, usually with a hydrogen-oxygen atom ratio of about 2:1. In some embodiments, the saccharide may include a structural formula of $C_6H_{12}O_6$.

In some embodiments, the chemical compound is incorporated in a pharmaceutical composition. The pharmaceutical composition may include a physiologically acceptable carrier or diluent.

In some embodiments, the lipofullerene-saccharide compound may be used in a method including therapeutically effective doses to inhibit the metastasis of neoplasms in mammals. In some embodiments, the method may include administering to a subject an effective amount of a pharmaceutically acceptable formulation including a lipofullerene-saccharide conjugate. The method may include inhibiting and/or ameliorating metastasis of neoplastic cells. The method may include inhibiting and/or ameliorating a malady associated with neoplastic cells. A subject may include a nonhuman mammal (e.g., an equine, canine, or feline). A subject may include a human.

In some embodiments, the neoplastic cells are malignant. In some embodiments, neoplastic cells may include pancreatic cancer cells, prostate cancer cells, lung cancer cells, breast cancer cells, colon cancer cells, and/or brain cancer cells.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
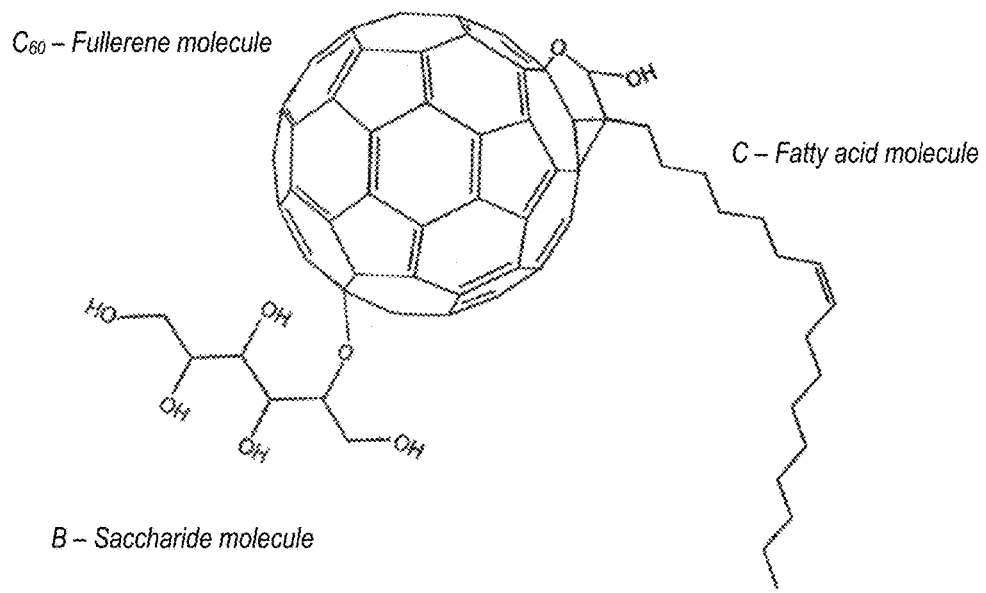
FIG. 1 depicts a proposed structure of an embodiment of a lipofullerene-saccharide conjugate.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning "having a feature that" performs the task or tasks during operation. As such, the component can be configured to perform the task even when the component is not currently on.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The terms "administration," "administering," or the like, as used herein when used in the context of providing a pharmaceutical, cosmeceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The term "animal" as used herein generally refers to any member of the kingdom Animalia, comprising multicellular organisms that have a well-defined shape and usually limited growth, can move voluntarily, actively acquire food and digest it internally, and have sensory and nervous systems that allow them to respond rapidly to stimuli: some classification schemes also include protozoa and certain other single-celled eukaryotes that have motility and animal like nutritional modes. Generally, the term animal as used herein does not refer to humans.

The term "anti-inflammatory" as used herein generally refers to a substance acting to reduce certain signs of inflammation (e.g., swelling, tenderness, fever, and pain).

The term "canine" as used herein generally refers to any of the biological family Canidae including carnivorous mammals including wolves, jackals, foxes, coyote, and the domestic dog.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The terms "effective concentration" or "effective amount" as used herein generally refers to a sufficient amount of the pharmaceutically active agent that is added to decrease, prevent or inhibit the growth of a virus and/or cancerous growth. The amount will vary for each compound and upon known factors related to the item or use to which the pharmaceutically active agent is applied.

The term "feline" as used herein generally refers to any of the biological family Felidae including lithe-bodied carnivorous mammals (as the lion, lynx, and cheetah, as well as the common house cat) having often strikingly patterned fur, comparatively short limbs with soft pads on the feet, usually sharp curved retractile claws, a broad and somewhat rounded head with short but powerful jaws equipped with teeth suited to grasping, tearing, and shearing through flesh, erect ears, and typically eyes with narrow or elliptical pupils and especially adapted for seeing in dim light.

The term "fullerene" as used herein generally refers to is a molecule of carbon in the form of a hollow sphere, ellipsoid, tube, and many other shapes.

The terms "in need of treatment" or "in need thereof" when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The term "lipid" as used herein generally refers to a substance of biological origin that is soluble in nonpolar solvents or more generally as hydrophobic or amphiphilic small molecules. Specific examples of lipids include fats, waxes, sterols, fat-soluble vitamins (e.g., vitamins A, D, E, and K), monoglycerides, diglycerides, triglycerides, and phospholipids.

The term "malady" as used herein generally refers to any disorder or disease of the body or any undesirable or disordered condition including, but not limited to, illness, sickness, affliction, complaint, ailment, indisposition, virus, disease, fungus, infection, disease, etc.

The term "mammal" as used herein generally refers to any vertebrate of the class Mammalia, having the body more or less covered with hair, nourishing the young with milk from the mammary glands, and, with the exception of the egg-laying monotremes, giving birth to live young. Generally, the term mammal as used herein does not refer to humans.

The term "metastasis" as used herein generally refers to the development of secondary malignant growths at a distance from a primary site of cancer.

The term "neoplasms" as used herein generally refers to an abnormal growth of tissue in some part of the body, especially as a characteristic of cancer.

The terms "oligomeric" and "polymeric" as used herein are generally used interchangeably herein to generally refer to multimeric structures having more than one component monomer or subunit.

Terms such as "pharmaceutical composition," "pharmaceutical formulation," "pharmaceutical preparation," or the like, are used herein to generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

The term "pharmacologically inert," as used herein, generally refers to a compound, additive, binder, vehicle, and the like, that is substantially free of any pharmacologic or "drug-like" activity.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

The term "saccharide" as used herein generally refers to a biological molecule consisting of carbon (C), hydrogen (H) and oxygen (O) atoms, usually with a hydrogen-oxygen atom ratio of about 2:1.

The term "subject" as used herein generally refers to a mammal (e.g., felines, canines), and in particular to a human.

The phrase "therapeutically effective amount" generally refers to an amount of a drug or pharmaceutical composition that will elicit at least one desired biological or physiological response of a cell, a tissue, a system, animal or human that is being sought by a researcher, veterinarian, physician or other caregiver.

Embodiments

Accordingly, there exists a need for an improved composition which inhibits and/or ameliorates metastasis of neoplasms in mammals this would be highly beneficial.

In some embodiments, a lipofullerene-saccharide compound and a method of inhibiting and/or ameliorating metastasis of neoplastic cells using said compound is disclosed herein. In some embodiments, the lipofullerene-saccharide compound may be formed by reacting (e.g., coupling) a lipid and a saccharide with a fullerene. In some embodiments, the lipofullerene saccharide may include a structural formula of $[C60]x[C6H12O6]y[C18H34O2]z$. x may be greater than or equal to 1, y may be greater than or equal to 1, and z may be greater than or equal to 1. FIG. 1 depicts an embodiment of a lipofullerene-saccharide conjugate.

Upon reviewing the results of the in vitro exposure of the various cancerous cell lines (specifics discussed herein), many of the C60 and LC60S ("lipofullerene-saccharide conjugate") based compositions have demonstrated an ability to mitigate the metastasis of a broad range of different types of cancers. In vitro experiments in some instances have demonstrated that C60 based compositions may inhibit metastasis of certain cancerous cell lines better than the LC60S based compositions. However, in vivo experiments detailed herein demonstrate that LC60S based compositions display a greater efficacy inhibiting the metastasis of cancers than C60 based compositions. This difference is theorized to be attributed to the saccharide coupled to the C60 allowing LC60S to penetrate deep within tumor masses in vivo (due to most cancers naturally absorbing saccharides for nutrients), while this benefit is not as obvious during in vitro tests as these tests typically involve small cell clusters at most.

Saccharides are theorized to be used as a targeting mechanism for effectively transporting the C60 and Serrapeptase to and/or within a tumor. In order for metastasis to occur the mitochondria have to be downregulated and it needs to produce super oxides. Compositions described herein may block the production of super oxides (e.g., using fullerene or fullerene derivatives. Compositions described herein may stop the replication of the cancer cells as a result at least in part to blocking production of super oxides. Compositions described herein may block the inflammatory markers (e.g., IL-6 and IL-8) as well, as is discussed in U.S. Pat. No. 9,308,243 to Mitchell et al. which is incorporated herein in its entirety.

In some embodiments, the fullerene may include C60. Fullerenes may include molecules of carbon in the form of a hollow sphere, ellipsoid, tube, and many other shapes. A fullerene is a molecule of carbon in the form of a hollow sphere, ellipsoid, tube, and many other shapes. Spherical fullerenes may be referred to as buckminsterfullerene or buckyballs or C60, and they resemble the balls used in soccer. Cylindrical fullerenes may be referred to as carbon nanotubes or buckytubes. Fullerenes are similar in structure to graphite, which is composed of stacked graphene sheets of linked hexagonal rings; but they may also contain pentagonal (or sometimes heptagonal) rings. Fullerenes are stable, but not unreactive. The $sp^2$-hybridized carbon atoms must be bent to form the closed sphere or tube, which produces angle strain. The characteristic reaction of fullerenes is electrophilic addition at 6,6-double bonds, which reduces angle strain by changing $sp^2$-hybridized carbons into $sp^3$-hybridized ones. The change in hybridized orbitals causes the bond angles to decrease from about 120° in the $sp^2$ orbitals to about 109.5° in the $sp^3$ orbitals. This decrease in bond angles allows for the bonds to bend less when closing the sphere or tube, and thus, the molecule becomes more stable.

Fullerenes have been used for several biomedical applications including the design of high-performance MM contrast agents, X-Ray imaging contrast agents, photodynamic therapy and drug and gene delivery. Research on fullerene toxicity beginning in the early 1990s to present appears to conclude that very little evidence gathered since the discovery of fullerenes indicates that C60 is toxic. The toxicity of these carbon nanoparticles appears to be not only dose and time-dependent, but also depends on a number of other factors such as: type (e.g., C60, C70, functional groups used to water solubilize these nanoparticles (e.g., OH, COOH), and method of administration (e.g., intravenous, intraperitoneal)).

In some embodiments, the lipid may include a fatty acid. A lipid may refer to a substance of biological origin that is soluble in nonpolar solvents or more generally as hydrophobic or amphiphilic small molecules. Specific examples of lipids may include fats, waxes, sterols, fat-soluble vitamins (e.g., vitamins A, D, E, and K), monoglycerides, diglycerides, triglycerides, and phospholipids. The main biological functions of lipids include storing energy, signaling, and acting as structural components of cell membranes. In some embodiments, the lipid may include a structural formula of C18H34O2. Other lipids have been examined but the current fatty acid had a more pronounced beneficial effect.

Lipids may be broadly defined as hydrophobic or amphiphilic small molecules. The amphiphilic nature of some lipids may allow them to form structures such as vesicles, multilamellar/unilamellar liposomes, or membranes in an aqueous environment. Biological lipids originate entirely or in part from two distinct types of biochemical subunits or "building-blocks" ketoacyl and isoprene groups. Using this approach, lipids may be divided into eight categories: fatty acids, glycerolipids, glycerophospholipids, sphingolipids, saccharolipids, polyketides, sterol lipids and prenol lipids.

Lipids may encompass molecules such as fatty acids and their derivatives (including tri-, di-, monoglycerides, and phospholipids), as well as other sterol-containing metabolites such as cholesterol. Although humans and other mammals use various biosynthetic pathways to both break down and synthesize lipids, some essential lipids cannot be made this way and must be obtained from the diet.

In some embodiments, one or more components of the chemical composition are suspended in and/or dissolved in at least one lipid. In some embodiments, at least one of the lipids may include olive oil. In some embodiments, at least one of the lipids may include mussel oil. In some embodiments, lipofullerene-saccharide compound may be suspended in a lipid at a concentration of about 0.1 to about 2.0 mg/ml or about 1.0 to about 1.6 mg/ml or preferentially about 1.2 to about 1.6 mg/ml. Concentrations of up to 3.6 mg/ml have been achieved but as of now concentrations of 2.0 mg/ml or greater do not seem to be as potent during testing as suspensions of the lower concentrations.

In some embodiments, the saccharide may include a sugar. A sugar may refer to a biological molecule consisting of carbon (C), hydrogen (H) and oxygen (O) atoms, usually with a hydrogen-oxygen atom ratio of about 2:1. In some embodiments, the saccharide may include a structural formula of C6H12O6. There are 21 different saccharide molecules which have the structural formula C6H12O6, but of all of these cancer cells have predominantly chosen to absorb fructose at a markedly higher rate than the other saccharides explaining the choice for the preferred embodiment. In some embodiments, saccharides may be administered as part of a pharmaceutical composition. Saccharides may be administered as part of a composition at a concentration of about 5 to about 50% by volume or preferentially about 5 to about 20% by volume.

In some embodiments, buckminsterfullerene (C60) is bound with a lipid base. The resulting lipofullerene may be catalytically treated with saccharides. The lipofullerene may be treated with saccharides in a ratio of concentrations that are greater than 0.01% and less than 100.00%.

In some embodiments, the chemical compound is incorporated in a pharmaceutical or chemical composition. The pharmaceutical composition may include a physiologically acceptable carrier or diluent (e.g., olive oil). In some embodiments, the composition may include an anti-inflammatory. An anti-inflammatory may include serratiopeptidase. Serratiopeptidase (*Serratia* E-15 protease, also known as serralysin, serrapeptase, serratiapeptase, serratia peptidase, serratio peptidase, or serrapeptidase) is a proteolytic enzyme (protease) produced by enterobacterium *Serratia* sp. E-15. This microorganism was originally isolated in the late 1960s from silkworm. In some embodiments, the lipofullerene saccharide may be formed using at least some ionic bonds. In some embodiments, the lipofullerene saccharide may be formed using covalent bonds. In some embodiments, the lipid and fullerene may form an adduct. The term "adduct" as used herein generally refers to a product of a direct addition of two or more distinct molecules, resulting in a single reaction product containing all atoms of all components. In some embodiments, the lipid and fullerene may form an ionic bond. In some embodiments, the lipid and fullerene may form a covalently bound compound. It is theorized that the lipid and fullerene form an adduct while the saccharide directly bonds to the fullerene.

In some embodiments, the lipofullerene-saccharide compound may be used in a method including therapeutically effective doses to inhibit the metastasis of neoplasms in mammals. In some embodiments, the method may include administering to a subject an effective amount of a pharmaceutically acceptable formulation including a lipofullerene-saccharide compound. The composition may be suspended in a lipid (e.g., olive oil). The composition may include anti-inflammatories (e.g., serrapeptase). The method may include inhibiting and/or ameliorating metastasis of neoplastic cells. The method may include inhibiting and/or ameliorating a malady associated with neoplastic cells. A subject may include a nonhuman mammal (e.g., an equine, canine, or feline). A subject may include a human.

In some embodiments, the neoplastic cells are malignant. In some embodiments, neoplastic cells may include pancreatic cancer cells, prostate cancer cells, lung cancer cells, breast cancer cells, colon cancer cells, and/or brain cancer cells.

In some embodiments, the method may include a specific administration regimen associated with administration of the compositions described herein. In some embodiments, subjects being administered the compositions described herein may be placed on a ketogenic diet. The ketogenic diet is a high-fat, adequate-protein, low-carbohydrate diet that in medicine is used primarily to treat difficult-to-control (refractory) epilepsy in children. The diet forces the body to burn fats rather than carbohydrates. Normally, the carbohydrates contained in food are converted into glucose, which is then transported around the body and is particularly important in fueling brain-function. However, if there is little carbohydrate in the diet, the liver converts fat into fatty acids and ketone bodies. The ketone bodies pass into the brain and replace glucose as an energy source. In some embodiments, the subject may be allowed to only eat a limited number of times per day (e.g., 1-2).

In some embodiments, the dosage of the composition may be administered at a different time from the subject's feeding (e.g., several hours or about 3 hours separation between feeding and dosing). This type of specific administration basically starves any cancer cells by withholding the cancer cell's preferred energy source of carbohydrates (specifically saccharides) so that the cancer cells are starving for nutrients and therefore more readily absorb the lipofullerene saccharide conjugate due to the saccharide.

In some embodiments, the method may include eliminating or at least limiting the administration of other commonly prescribed medications associated with cancer (e.g., pain medications) which may interfere with absorption of the fullerene derivatives described herein (due to competition).

In some embodiments, a method may include administering to a subject an effective amount of a pharmaceutically acceptable formulation comprising the chemical composition. The method may include inhibiting and/or ameliorating inflammation and/or a malady associated with inflammation. In some embodiments, the subject may include a human or a nonhuman mammal. Nonhuman mammals may include equines, canines, or felines.

In some embodiments, a chemical composition may elicit an anti-inflammatory response. The chemical composition may elicit an anti-inflammatory response in subjects. The chemical composition may elicit an anti-inflammatory response in joints and muscles, improves immunity and/or helps remove scar tissue.

In some embodiments, a chemical composition may include one or more lipofullerene saccharides.

In some embodiments, a chemical composition may include buckminsterfullerene (Carbon 60 (C60)). C60 may function as an anti-oxidant and/or free radical scavenger assisting in maintaining good health. Fullerene C60 may function to inactivate hydroxyl radicals by attaching to the double bonds. The majority of reactive oxygen species (ROS) may be generated in mitochondrial respiratory chain and the presence of C60 inside the cells helps remove ROS.

Dosage and Administration

In some embodiments, chemical compositions described herein may be administered at a dosage level up to conventional dosage levels, but will typically be less than about 50 mL per day. Suitable dosage levels for chemical compositions described herein may be about 0.01 mg to 10 mg per kg body weight of the patient per day, from about 0.1 mg to 1 mg per kg body weight of the patient per day, or from about 0.01 mg to 0.1 mg per kg body weight of the patient per day. The compound may be administered on a regimen of up to 6 times per day, between about 1 to 4 times per day, or once per day.

In the case where an oral composition is employed, a suitable dosage range is, e.g. from about 0.01 mg to about 10 mg per kg of body weight per day, preferably from about 0.1 mg to about 0.5 mg per kg.

It will be understood that the dosage of the therapeutic agents will vary with the nature and the severity of the condition to be treated, and with the particular therapeutic agents chosen. The dosage will also vary according to the age, weight, physical condition and response of the individual patient. The selection of the appropriate dosage for the individual patient is within the skills of a clinician.

In addition to administering chemical compositions described herein as described, the compounds may be administered as part of a pharmaceutical preparation containing suitable pharmaceutically acceptable carriers, preservatives, excipients and auxiliaries which facilitate processing of the chemical compositions described herein which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailability as described above, together with the excipient. While individual needs may vary, determination of the optimal ranges of effective amounts of each component is within the skill of the art.

General guidance in determining effective dose ranges for pharmacologically active compounds and compositions for use in the presently described embodiments may be found, for example, in the publications of the International Conference on Harmonisation and in REMINGTON'S PHARMACEUTICAL SCIENCES, $8^{th}$ Edition Ed. Bertram G. Katzung, chapters 27 and 28, pp. 484-528 (Mack Publishing Company 1990) and yet further in BASIC & CLINICAL PHARMACOLOGY, chapters 5 and 66, (Lange Medical Books/McGraw-Hill, N.Y., 2001).

Pharmaceutical Compositions

Chemical compositions described herein are typically administered orally but any suitable route of administration may be employed for providing a subject with an effective dosage of drugs of the chemical compositions described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally.

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the drugs used in the present invention are conveniently delivered in the form of an aerosol spray presentation from pressurized packs or nebulisers. The compounds may also be delivered as powders which may be formulated and the powder composition may be inhaled with the aid of an insufflation powder inhaler device.

Suitable topical formulations for use in the present embodiments may include transdermal devices, aerosols, creams, ointments, lotions, dusting powders, gels, and the like.

In practical use, drugs used can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives. Optionally, the resulting mixture may be ground and processed. The resulting mixture of granules may be used, after adding suitable auxiliaries, if desired or necessary, to obtain tablets, softgels, lozenges, capsules, or dragee cores.

The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

Liquid dosage forms for oral administration can contain coloring and flavoring to increase subject acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

In some embodiments, an oral composition may include a flavoring. A flavoring may include something an animal may find palatable. For example a flavoring may include malt extract, xylitol, splenda, sucralose or any sweetener. A flavoring may range from 0.01% to 0.10%, 0.10% to 1.0%, or 1.0% to 10.0% of a composition.

In some embodiments, a composition may include a colorant. A colorant may include D&C Blue #1 or any FDA approved color. A colorant may range from 0.001% to 0.010%, 0.010% to 0.10%, or 0.10% to 1.0% of a composition.

Additional oral compositions which may be used to deliver chemical compositions described herein, as well as additional uses, are described in U.S. Pat. No. 4,666,896 to Warner, Jr. et al., U.S. Pat. No. 5,393,516 to Rheinberger et al., and U.S. Pat. No. 5,948,390 to Nelson et al., as well as U.S. Patent Publication No. 2005/0158252 to Romanowski et al., which are incorporated by reference as if fully set forth herein.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas. Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include, but are not limited to, suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Liposomal formulations, in which mixtures of the chemical compositions described herein with, for example, egg yolk phosphotidylcholine (E-PC), may be made for injection. Optionally, the suspension may contain stabilizers, for example, antioxidants such as BHT, and/or preservatives, such as benzyl alcohol.

In some embodiments, an oral composition may include a fragrance.

In some embodiments, a composition may include additional additives which may function in combination or separately from the chemical compositions described herein in solution. Additives may function to improve a subject's health. Additives may include vitamins including, but not limited to, vitamins D and E.

In some embodiments, different compositions may be formulated for different types of users. For professionals users (e.g., doctors, vetenaries), compositions may include a greater percentage of chemical compositions described herein than compositions formulated for over the counter sale to nonprofessionals. Professional compositions may not include flavorings or colorants.

Examples

Having now described the invention, the same will be more readily understood through reference to the following example(s), which are provided by way of illustration, and are not intended to be limiting of the present invention.

In some embodiments, buckminsterfullerene (C60) is bound with a lipid base. The resulting lipofullerene may be catalytically treated with saccharides. The lipofullerene may be treated with saccharides in a ratio of concentrations that are greater than 0.01% and less than 100.00%.

Embodiments of compounds described herein were evaluated against cancer cells in vivo. In order to obtain clinically accurate models, the technique of surgical orthotopic implantation (SOI) was used to transplant histologically-intact fragments of human cancer, including tumors taken directly from the patient, to the corresponding organ of immune deficient rodents.

The technique of surgical orthotopic implantation (SOI) in mouse was developed to transplant histologically-intact fragments of human cancer. Advantages of orthotopic models include use of the relevant site for tumor-host interactions, the emergence of disease-relevant metastases, the ability to study site-specific dependence of therapy, organ-specific expression of genes and that clinical scenarios can be replicated (e.g., surgical removal of primary tumor or adjuvant therapy of occult metastasis). The SOI model has been demonstrated to be a clinically relevant orthotopic model. The use of GFP gave significant added power to the SOI model, enabling the observation of metastasis at the single cell level. A major advantage of GFP expressing tumor cells is that imaging requires no preparative procedures, contrast agents, substrates, anesthesia, or light-tight boxes as do other imaging techniques. GFP imaging is thus uniquely suited for whole-body imaging of tumor growth and metastases in live animals.

The study referenced herein utilized the BxPC-3 pancreatic tumor cell line transfected with green fluorescent protein (GFP). BxPC-3 was used because it exhibits a high degree of metastatic behavior. Pancreatic adenocarcinoma (PA) or pancreatic cancer is an aggressive disease that develops in a relatively symptom-free manner and is usually advanced at the time of diagnosis. Pancreatic cancer is the fourth leading cause of cancer deaths, being responsible for 7% of all cancer-related deaths in both men and women. According to the American Cancer Society, for all stages of pancreatic cancer combined, the one-year relative survival rate is 20%, and the five-year rate is 6%. Reasons for low survival in this disease include aggressive tumor biology, high metastatic potential, and late presentation at the time of diagnosis. Therefore, effective new drugs are urgently needed for treating the lethal pancreatic cancer. The inclusion of GFP expression in the in vivo model allowed for visualization and imaging of tumor growth and metastasis, a critically important factor for the understanding and treatment of metastatic processes.

BxPC-3 cell line, Human primary pancreatic adenocarcinoma, derived from a 61 year old female with a primary adenocarcinoma of the pancreas. Transgenic tumor models, or subcutaneously growing human tumors in immune-deficient mice, do not sufficiently represent clinical cancer, especially with regard to metastasis and drug sensitivity. The BxPC-3 human pancreatic cancer cell line that was used for this study was obtained from the American Type Culture Collection (ATCC, Rockville, Md.).

Comparison of the SOI models with transgenic mouse models of cancer indicate that the SOI models have more features of clinical metastatic cancer. Cancer cell lines have been stably transfected with the jellyfish Aequorea victoria green fluorescent protein (GFP) in order to track metastases in fresh tissue at ultra-high resolution and externally image metastases in the SOI models. These unique SOI models have been used for innovative drug discovery and mechanism studies and serve as a bridge linking pre-clinical and clinical research and drug development.

The RetroXpress vector pLEIN was purchased from Clontech Laboratories, Inc. (Palo Alto, Calif.). The pLEIN vector expresses enhanced GFP and the neomycin resistance gene on the same bicistronic message, which contains an IRES site. pLEIN was produced in PT67 packaging cells. BxPC-3 cells were transduced with supernatants of the pLEIN-producing PT67 cells. Stable high-expression GFP transductants were selected in neomycin by Anticancer, Inc. Orthotopic human pancreatic cancer xenografts were established in nude mice by direct injection of fluorescent BxPC- 3-GFP tumor cells into the pancreas subcutaneously. A Leica stereo microscope MZ 12 equipped with a mercury bulb as a light source was used for the imaging experiments. Selective excitation of GFP was produced through a D425/60 band-pass filter and a 470 DCXR dichroic mirror. Fluorescence was emitted through a GG475 long-pass filter (Chroma Technology, Brattleboro, Vt.) and collected by a Hamamatsu Color Cooled CCD Video Camera HM C5810. High-resolution images were captured and processed with a Pro-Series Frame-Grabber and acquired by a Pentium-IV PC with Image Pro Plus 3.1 software (Media Cybernetics, Silver Spring, Md.)

The treatment of the test article (compound/compositions described herein) was started after 5 weeks of surgical orthotopic implantation (SOI), dated Jun. 9, 2014. At the first day of the treatment, Jul. 17, 2014 (day 1), the weight of the mouse was 34.1 grams and the pancreatic tumor size was 108 mm3.

In embodiments described herein, the C60 is first lipolized using various fatty acids and then conjugated using saccharides. The serum was given to the mice in a therapeutic level, 0.004 ml/gram of body weight.

The in vivo results on the orthotropic mouse model of metastatic pancreatic cancer after treatment with compounds/compositions described herein has resulted in controlling the tumor growth rate and more importantly metastasis has been prevented and the results are discussed here. In FIG. 1, a structural depiction of the lipofullerene-saccharide conjugate is proposed. The lipofullerene-saccharide conjugate formula is believed to be: [C60]x[C6H12O6]y[C18H34O2]z wherein x, y and z≥1.

Figure 2:
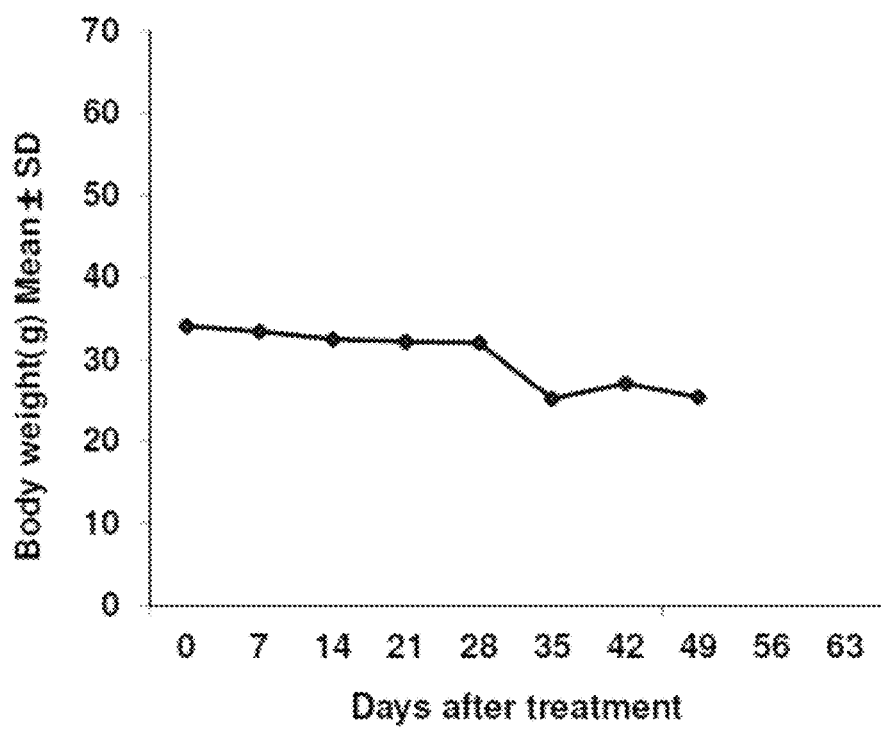
FIG. 2 depicts a graphical representation of a plot of the body weight against the number of days after initiation of the treatment.

In FIG. 2, the weight (grams) of the mice is plotted against the days after test article treatment has been started. The initial weight of the mice after 5 weeks of implantation (day 0 after the test article treatment) is 34.1 g. At the end of the treatment cycle of 7th week, the weight of the mice was 25.4 gram a decrease of 26%. The decrease in weight indicates that there is no unusual weight gain that normally happens due to metastasis.

Figure 3:
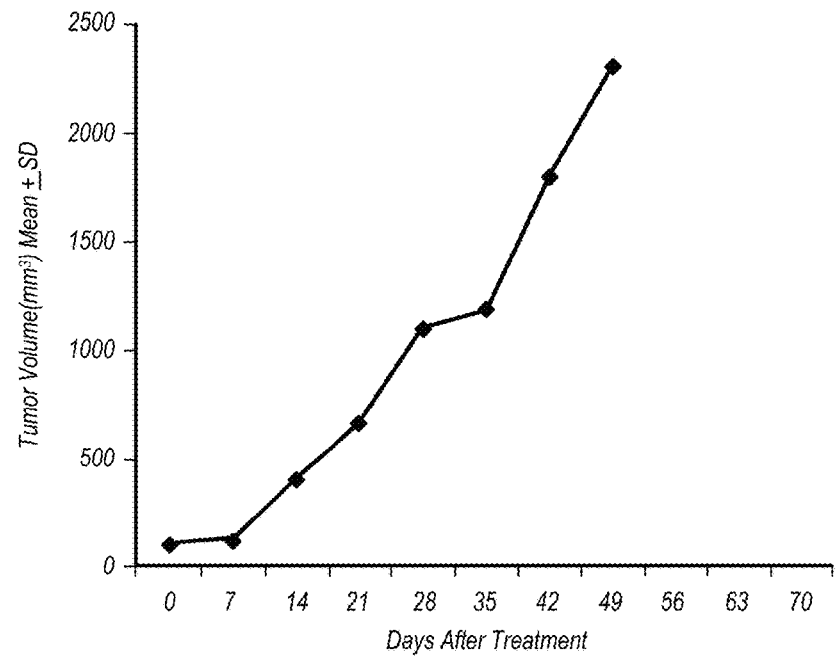
FIG. 3 depicts a graphical representation of a plot of volume of the tumor against the number of days after initiation of the treatment.
Figures 4A, 4B:
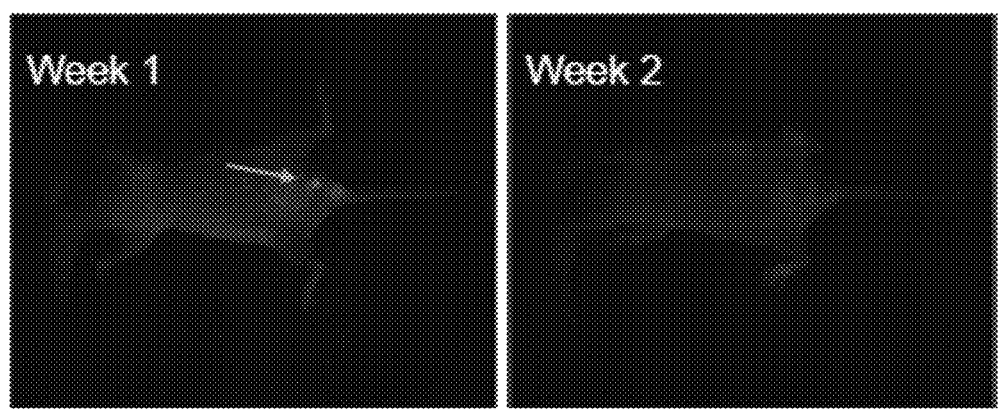
FIGS. 4A-F depict weekly whole body images. At the starting of the treatment (day 0), the tumor volume (Bx-Pc3 Human Pancreatic cancer) was 108 mm3 and the tumor was 5 weeks old. After 6 weeks of treatment, against typical precedent the primary tumor has not metastasized, but reached tumor burden in the location of implantation.
Figure 4C:
Figure 4D:
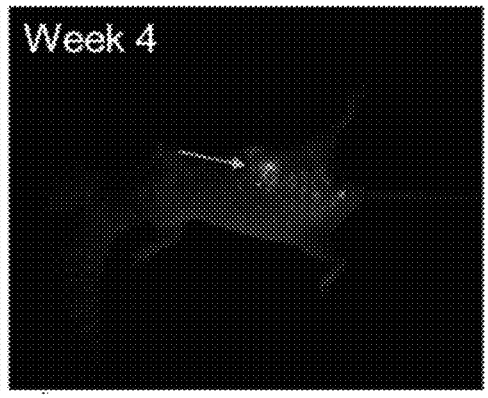
Figure 4E:
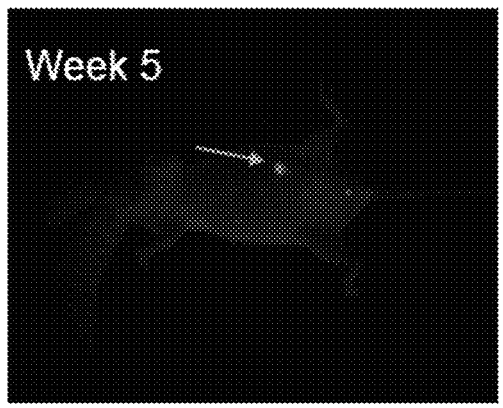
Figure 4F:
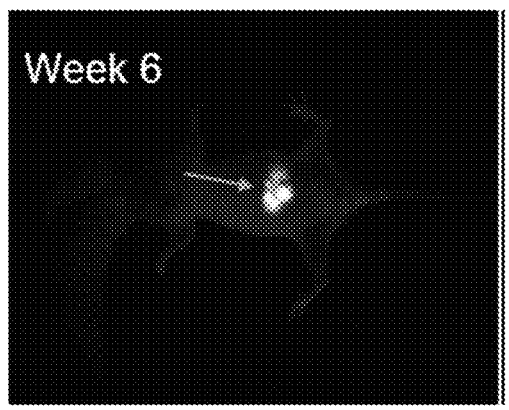

In FIG. 3, the primary tumor volume (mm3) is plotted against the days after treatment has been started. The initial volume of the tumor after 5 weeks of implantation (day 0 of the treatment) is 108 mm3. At the end of the treatment cycle of 7th week (after the test article treatment), volume of the tumor was 2304 mm3. The treatment dose was 0.004 ml of test article per gram of mice for the initial 3 days and 0.004 ml of test article per gram of mice every other day until the end of the treatment period. It is believed that, the dosage was just enough to act against the antimetastasis and not enough available to content the primary tumor. This may be the reason why there is an increase in the primary tumor size and of course even this lower amount of the test article is enough to arrest the metastatic events as observed in the last week.

Figure 5A:
FIGS. 5A-I depict weekly whole body images. After 6.5 weeks of treatment, against typical precedent the primary tumor (Pc3 Human Prostate cancer) has not metastasized, but reached tumor burden in the location of implantation.
Figure 5B:
Figure 5C:
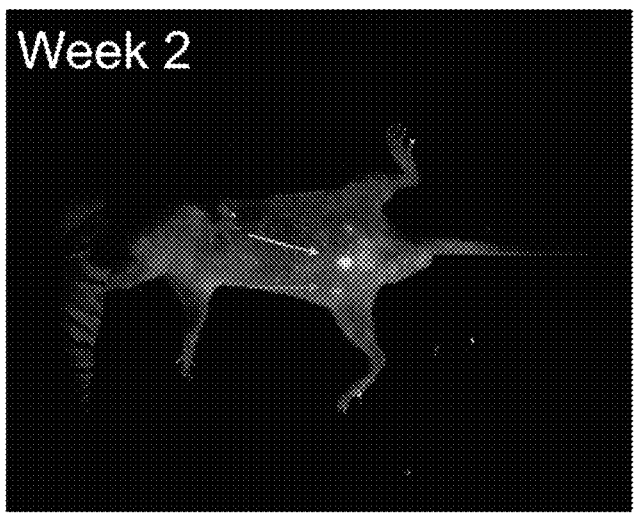
Figure 5D:
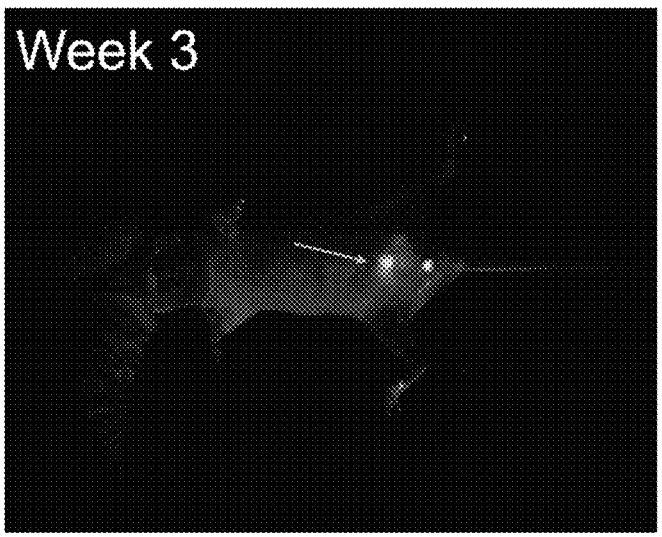
Figure 5E:
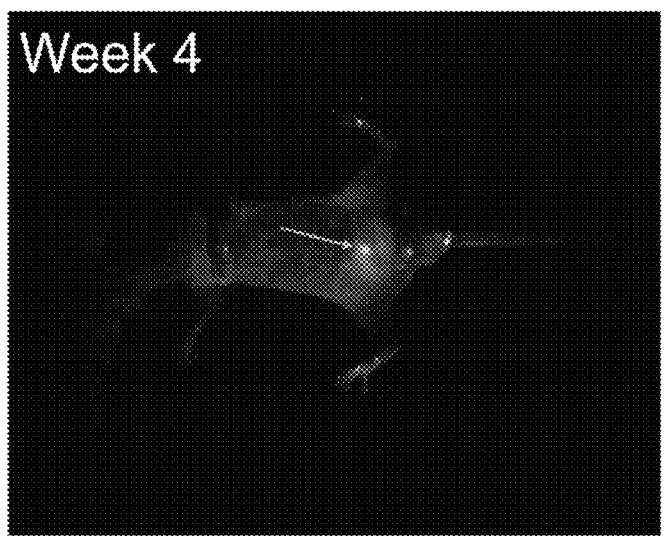
Figure 5F:
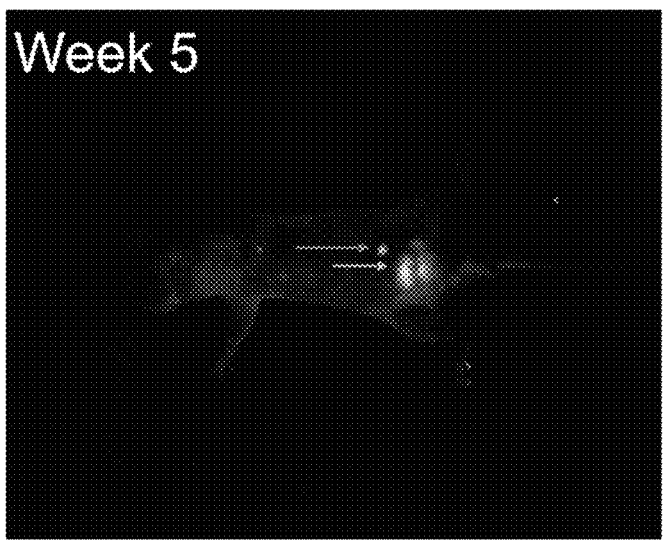
Figure 5G:
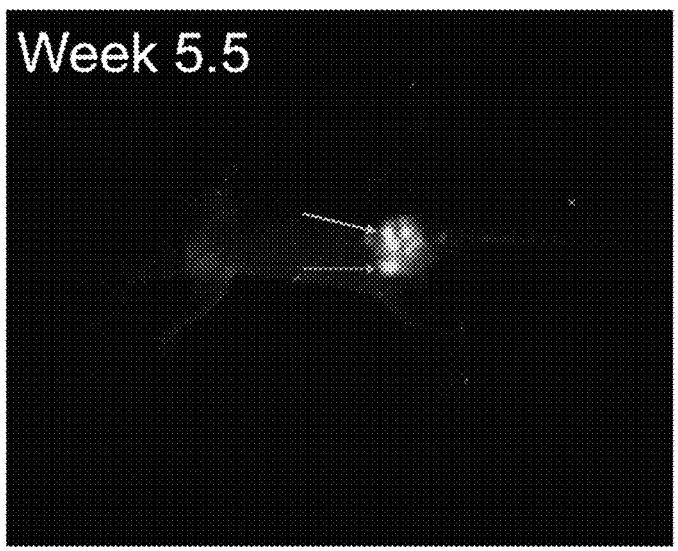
Figure 5H:
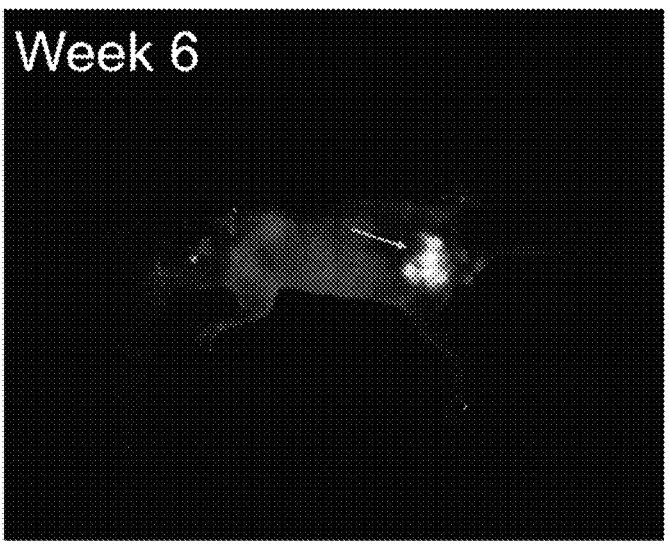
Figure 5I:
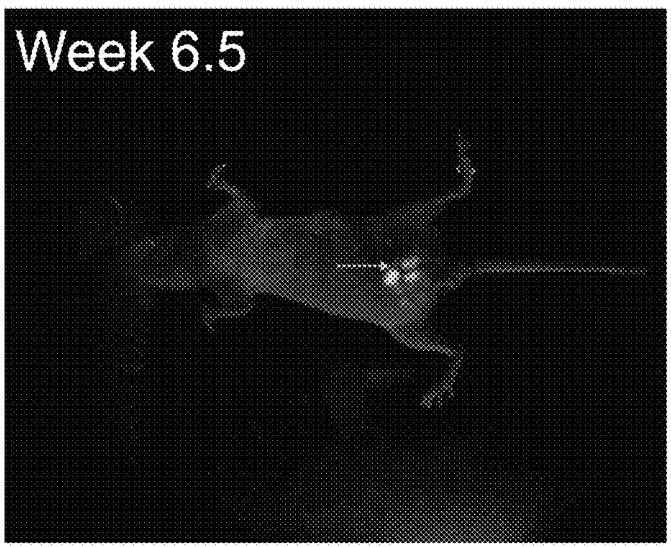
Figure 6:
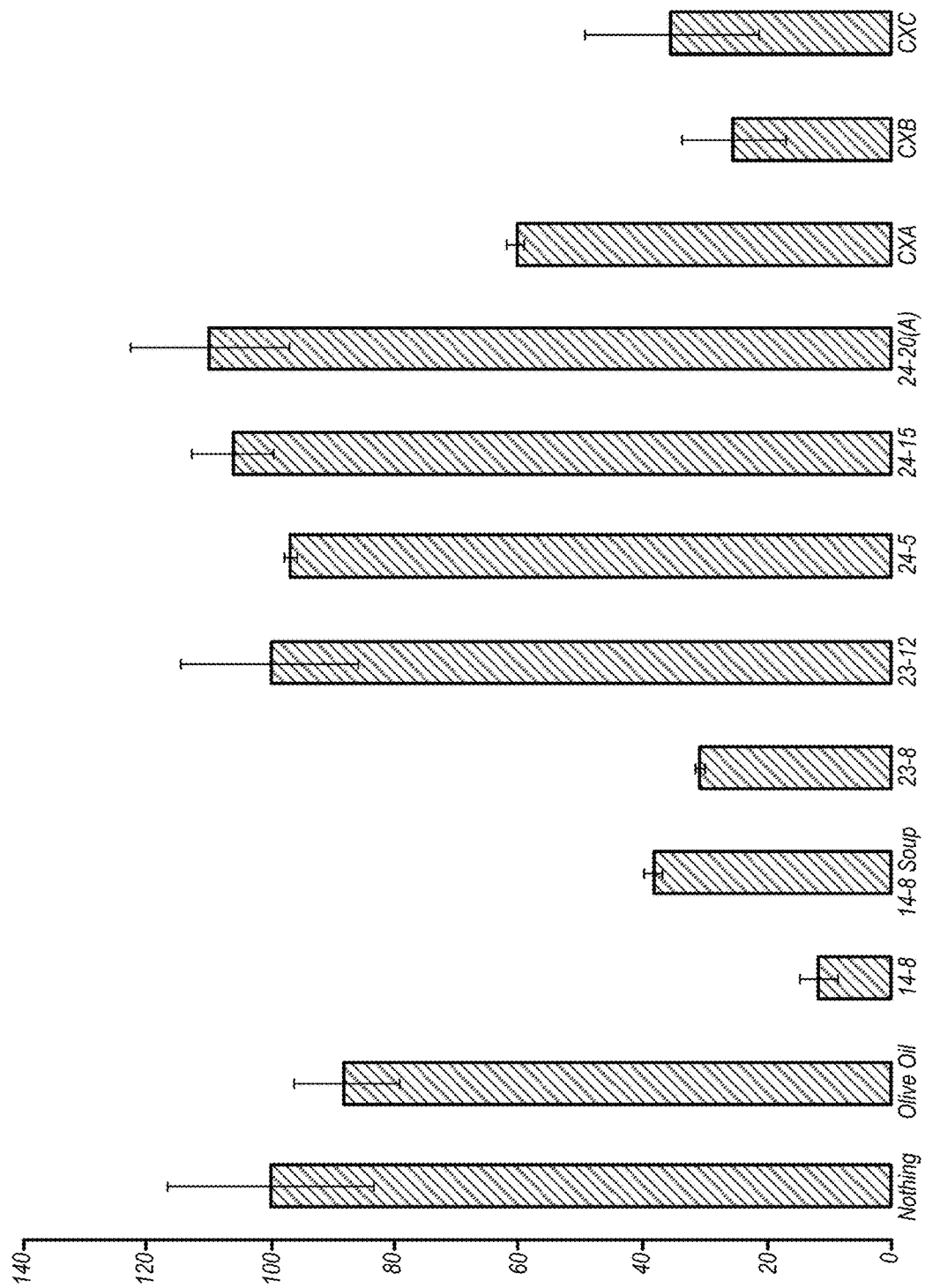
FIG. 6 depicts a graphical representation of a viability of a Pc3 human prostate (adenocarcinoma) cell line verses serval different compound and compositions relative to untreated cell lines as well as solvent (e.g., olive oil).
Figure 7:
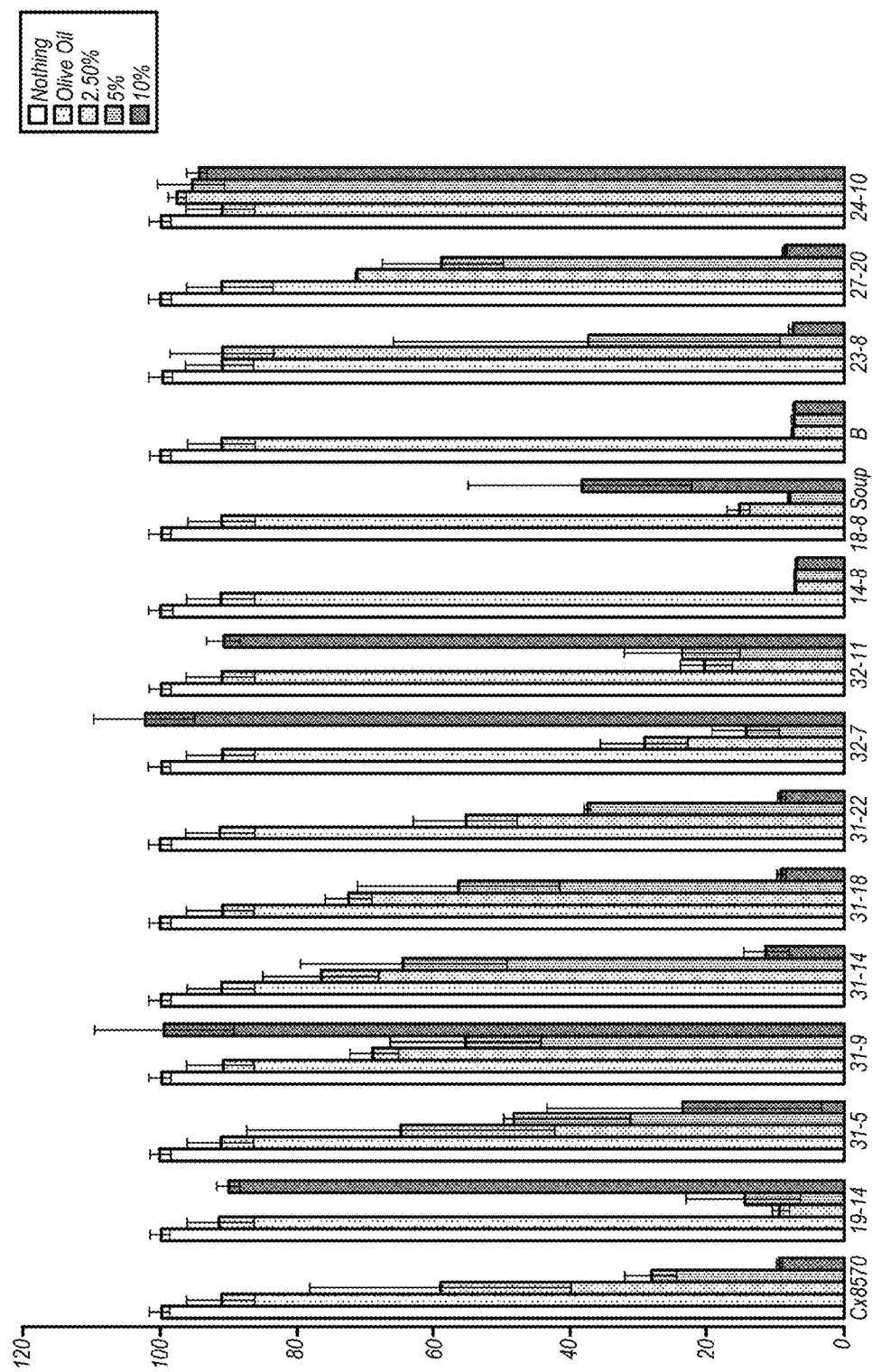
FIG. 7 depicts a graphical representation of a viability of a Pc3 human prostate (adenocarcinoma) cell line verses serval different compound and compositions relative to untreated cell lines as well as solvent (e.g., olive oil).
Figure 8:
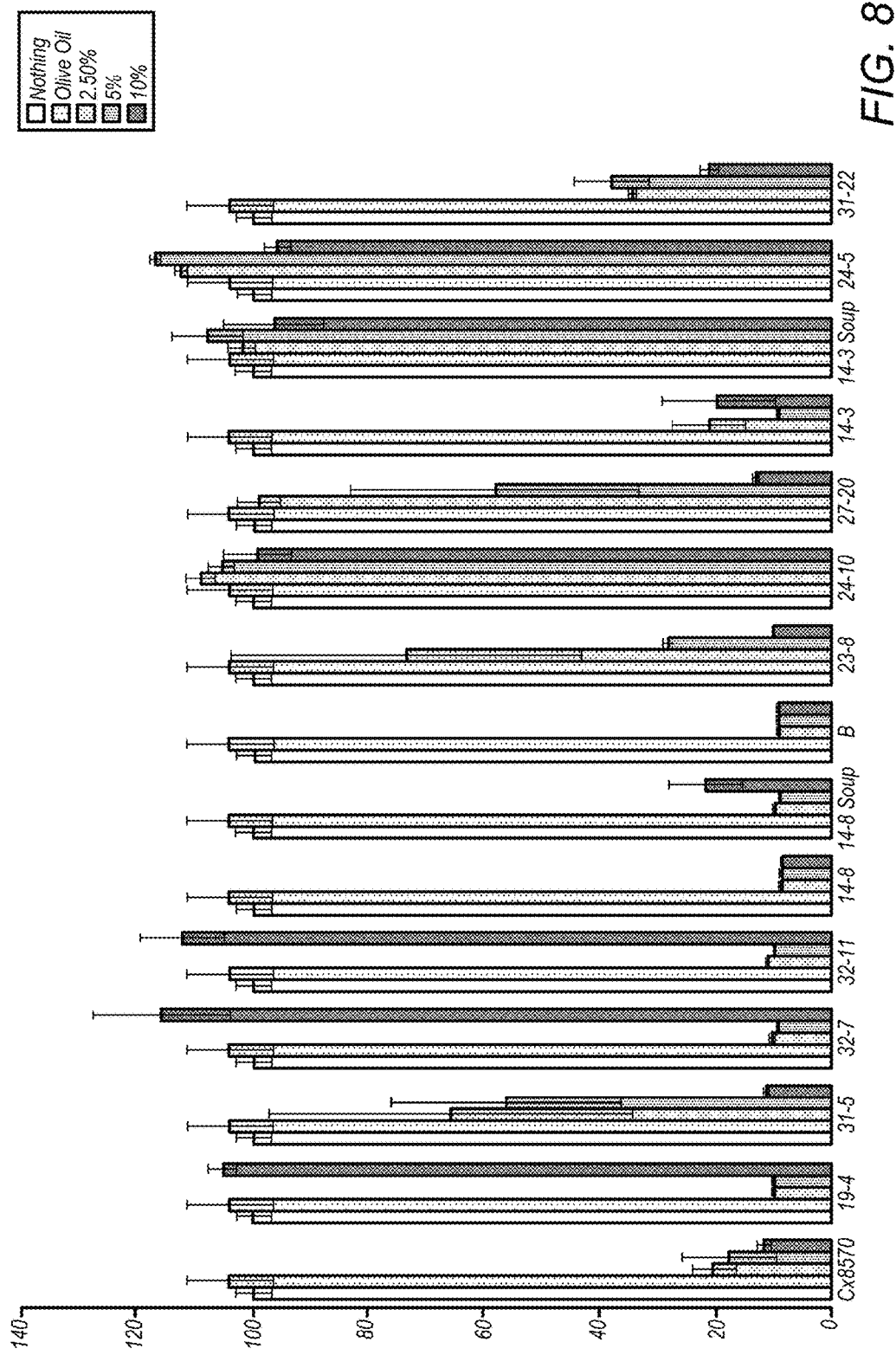
FIG. 8 depicts a graphical representation of a viability of a Pc3 human prostate (adenocarcinoma) cell line verses serval different compound and compositions relative to untreated cell lines as well as solvent (e.g., olive oil).
Figure 9:
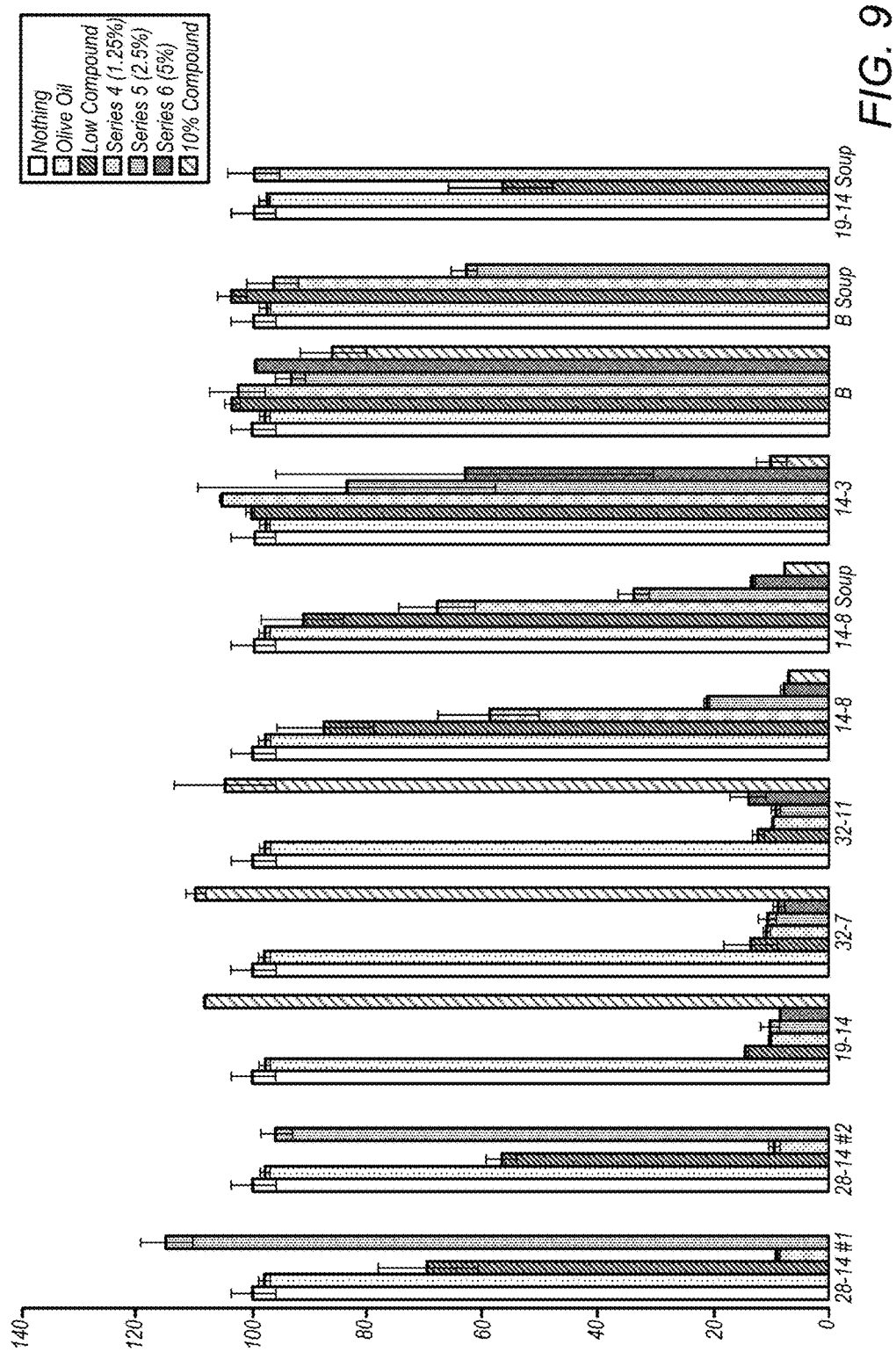
FIG. 9 depicts a graphical representation of a viability of a Pc3 human prostate (adenocarcinoma) cell line verses serval different compound and compositions at a variety of different concentrations relative to untreated cell lines as well as solvent (e.g., olive oil).

In FIGS. 4A-F, fluorescence microscopy images are presented. The fluorescent protein (GFP) is attached to the primary BxPC-3 cells and as the cell multiplies the GFP gets multiplied and gives rise to bright green fluorescence. The first image (FIG. 4A) is the first week after test article treatment and the primary tumor can be seen and the measurement corresponds to 108 mm3. The second week image (FIG. 4B) also contains the tumor and the size is measured to be 126 mm3. The consecutive weeks images are present (FIGS. 4C-4F) and as the time goes by, the tumor size increases as can be seen from the pictures. Surprisingly, the local and distant sites including liver, lungs, spleen, retroperitoneum, portal nodes, diaphragm, small intestine, colon, kidney and mediastinum did not have any tumor and thus no metastasis occurred. It should be noted that multiple metastatic events in a pancreatic cancer orthotopic model is very common. As can be seen from FIG. 4 images, there were no metastatic events observed on the test article treated mouse indicating the therapeutic nature of the test article. Furthermore, the described study is the first to demonstrate slowing down of the pancreatic cancer tumor and stop metastasis in BxPC-3 SOI mouse with the serum containing C60 and fructose treated olive oil. FIGS. 5A-I depict weekly whole body images. After 6.5 weeks of treatment, against typical precedent the primary tumor (Pc3 Human Prostate cancer) has not metastasized, but reached tumor burden in the location of implantation. The mouse images show weeks 0-6.5 with human prostate cancer (Pc3) and show a tremendous drop in the last 3 days terminating at week 6.5. The points of metastasis go away prior to the large reduction in activity in the primary tumor. FIG. 5I I depicts week 6.5 for the Pc-3. FIG. 5I demonstrates the rapid decrease of the primary tumor post-administration.

The SOI model has been demonstrated to be a clinically relevant orthotopic model. The use of GFP gave significant added power to the SOI model, enabling the observation of metastasis at the single cell level. The anti-metastatic efficacy of the test article (Cx8570 from LivePet, LLC) in this SOI model, therefore, is all the more impressive because the publications have unequivocally proven that high metastasis frequencies in the untreated animals could be detected with the ultra-high-resolution of GFP. Overall, the test article is capable of inhibiting BxPC-3 cell proliferation, cell cycle arrest, apoptosis induction and tumor anti-angiogenesis.

14-8 is EVOO+0.08% C60+500K SPU's of serratiopeptidase+1 g of L-Carnosine+10 mg's of ALA,GLU,ASP,GLY tetrapeptide per 100 mL's of solution (This is the Companion 60 formulation)

14-8 Soup: Is the residue resulting after centrifuging the composition 14-8 and removing the supernatant 23-8 is EVOO+0.12% LC60S ("lipofullerene-saccharide conjugate")+500K SPU's of serratiopeptidase mixed into suspension with saccharides @10% by volume per 100 mL's of solution 23-12 is EVOO+0.08% LC60S+500K SPU's of serratiopeptidase mixed into suspension with saccharides @40% by volume per 100 mL's of solution 24-5 is EVOO+500K SPU's of serrapeptase per 100 mL's of solution 24-15 is caprylic acid base with 0.04% Carbon 60+500K SPU's of serratiopeptidase per 100 mL's of solution 24-20(A) is EVOO+0.08% LC60S+750K SPU's of serratiopeptidase per 100 mL's of solution (stirred 0.5 hours)

CxA is EVOO+0.08% LC60S+500K SPU's of serratiopeptidase mixed into suspension with saccharides @10% by volume per 100 mL's of solution CxB is EVOO+0.08% LC60S+500K SPU's of serratiopeptidase mixed into suspension with saccharides @10% by volume+5 mL's of Gamma E oil per 100 mL's of solution CxC is EVOO+0.08% LC60S+500K SPU's of serratiopeptidase mixed into suspension with saccharides @10% by volume+5 mL's of Gamma E oil+2 mL's of J per 100 mL's of solution Cx8570 is EVOO+0.08% LC60S+500K SPU's of serratiopeptidase mixed into suspension with saccharides @10% by volume per 100 mL's of solution 19-14 is EVOO+0.08% C60

19-14 Soup: Is the residue resulting after centrifuging the composition 19-14 and removing the supernatant 31-5 is EVOO+0.08% LC60S+500K SPU's of serratiopeptidase mixed into suspension with saccharides @10% by volume per 100 mL's of solution 31-9 is EVOO+0.08% LC60S+750K SPU's of serratiopeptidase mixed into suspension with saccharides @10% by volume per 100 mL's of solution 31-14 is EVOO+0.08% LC60S+250K SPU's of serratiopeptidase mixed into suspension with saccharides @10% by volume per 100 mL's of solution 31-18 is EVOO+0.08% LC60S+125K SPU's of serratiopeptidase mixed into suspension with saccharides @10% by volume per 100 mL's of solution 31-22 is EVOO+0.08% LC60S+75K SPU's of serratiopeptidase mixed into suspension with saccharides @10% by volume per 100 mL's of solution 32-7 is EVOO+0.08% LC60S+500K SPU's of serratiopeptidase+1 g of L-Carnosine per 100 mL's of solution 32-11 is EVOO+0.08% LC60S+500K SPU's of serratiopeptidase per 100 mL's of solution!

B—is EVOO with 0.08% Carbon 60 by volume

Figure 10:
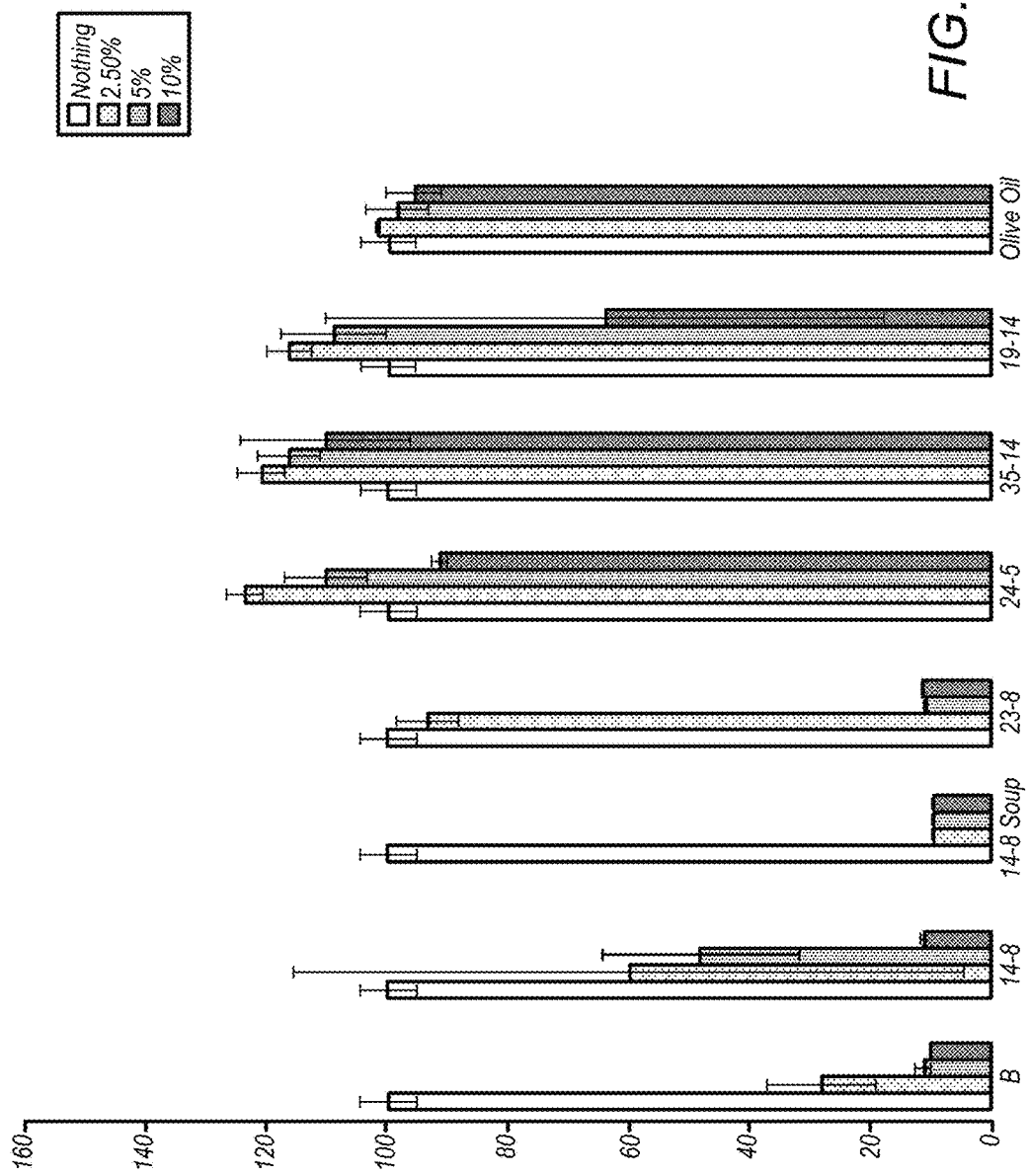
FIG. 10 depicts a graphical representation of a cytotoxicity for a Pc3 human prostate (adenocarcinoma) cell line verses serval different compound and compositions.

B Soup: Is the residue resulting after centrifuging the composition B and removing the supernatant 27-14 is EVOO+0.08% LC60S+500K SPU's of serratiopeptidase mixed into suspension with saccharides @10% by volume+0.5 g of L-Carnosine per 100 mL's of solution 27-20 is EVOO+0.08% LC60S+500K SPU's of serratiopeptidase mixed into suspension with saccharides @10% by volume+0.5 g of L-Carnosine+10 mg's of ALA,GLU,ASP,GLY tetrapeptide per 100 mL's of solution 24-10 is distilled water+500K SPU's of serratiopeptidase 100 mL's of solution 14-3 is Extra Virgin Olive Oil (EVOO)+0.08% LC60S+250K SPU's of serratiopeptidase+0.5 g of L-Carnosine+10 mg's of ALA,GLU,ASP,GLY tetrapeptide per 100 mL's of solution 28-14 #1 is EVOO+0.08% LC60S 100 mL's of solution 28-14 #2 is EVOO+0.08% LC60S 100 mL's of solution FIGS. 6-9 depict graphical representations of a viability of a Pc3 human prostate (adenocarcinoma) cell line verses serval different compound and compositions relative to untreated cell lines as well as solvent (e.g., olive oil). FIG. 10 depicts a graphical representation of a cytotoxicity for a Pc3 human prostate (adenocarcinoma) cell line verses serval different compound and compositions. As is demonstrated in FIGS. 6-10 lipofullerene-saccharide conjugate based compositions (e.g., 23-8) demonstrate an efficacy against human prostate cancer.

Figure 11:
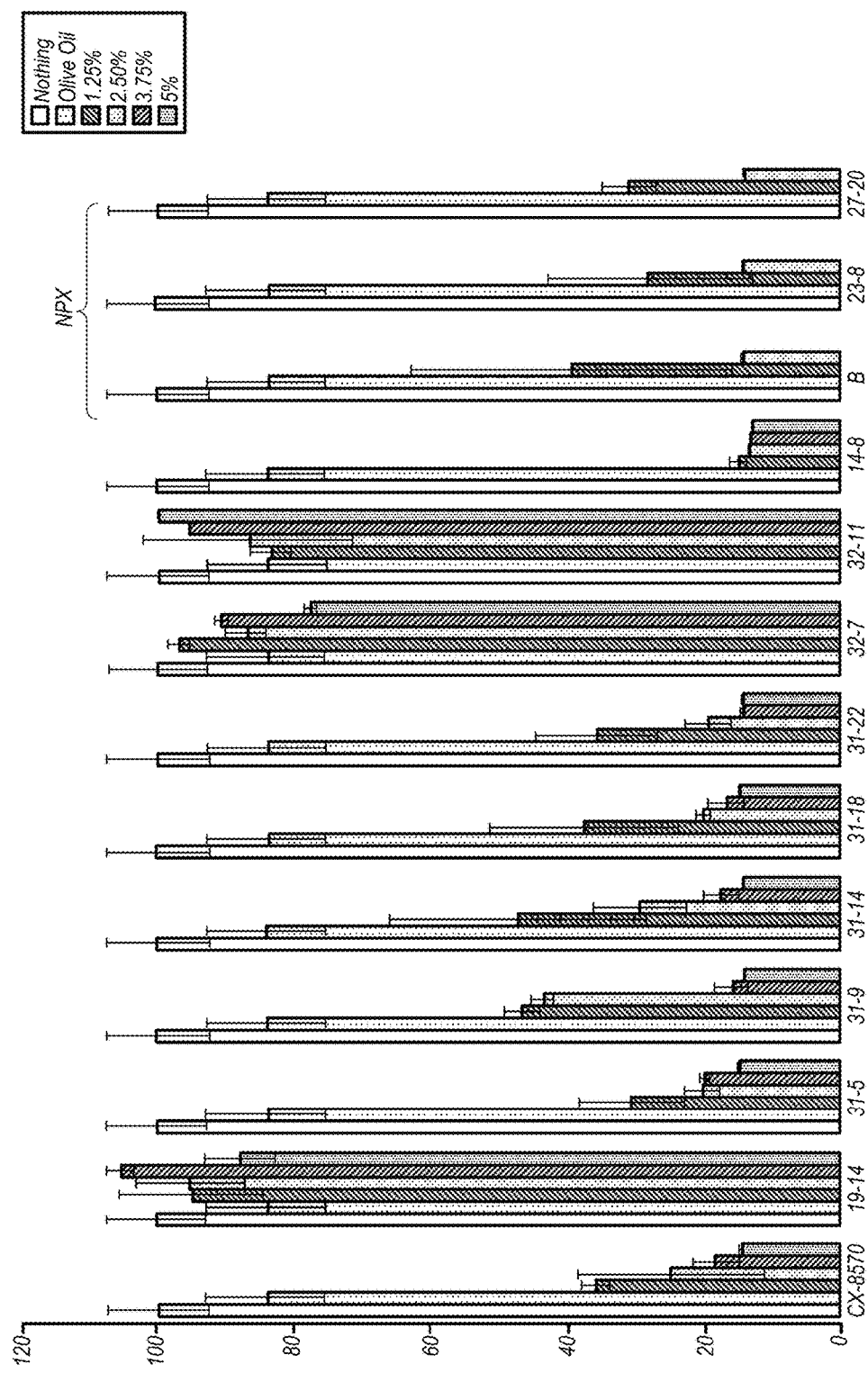
FIG. 11 depicts a graphical representation of a viability of a H293 human kidney cell line verses serval different compound and compositions at a variety of different concentrations relative to untreated cell lines as well as solvent (e.g., olive oil).

FIG. 11 depicts a graphical representation of a viability of a H293 human kidney cell line verses serval different compound and compositions at a variety of different concentrations relative to untreated cell lines as well as solvent (e.g., olive oil). As is demonstrated in FIG. 11 lipofullerene-saccharide conjugate based compositions (e.g., 23-8) demonstrate an efficacy against human kidney cancer.

Figure 12:
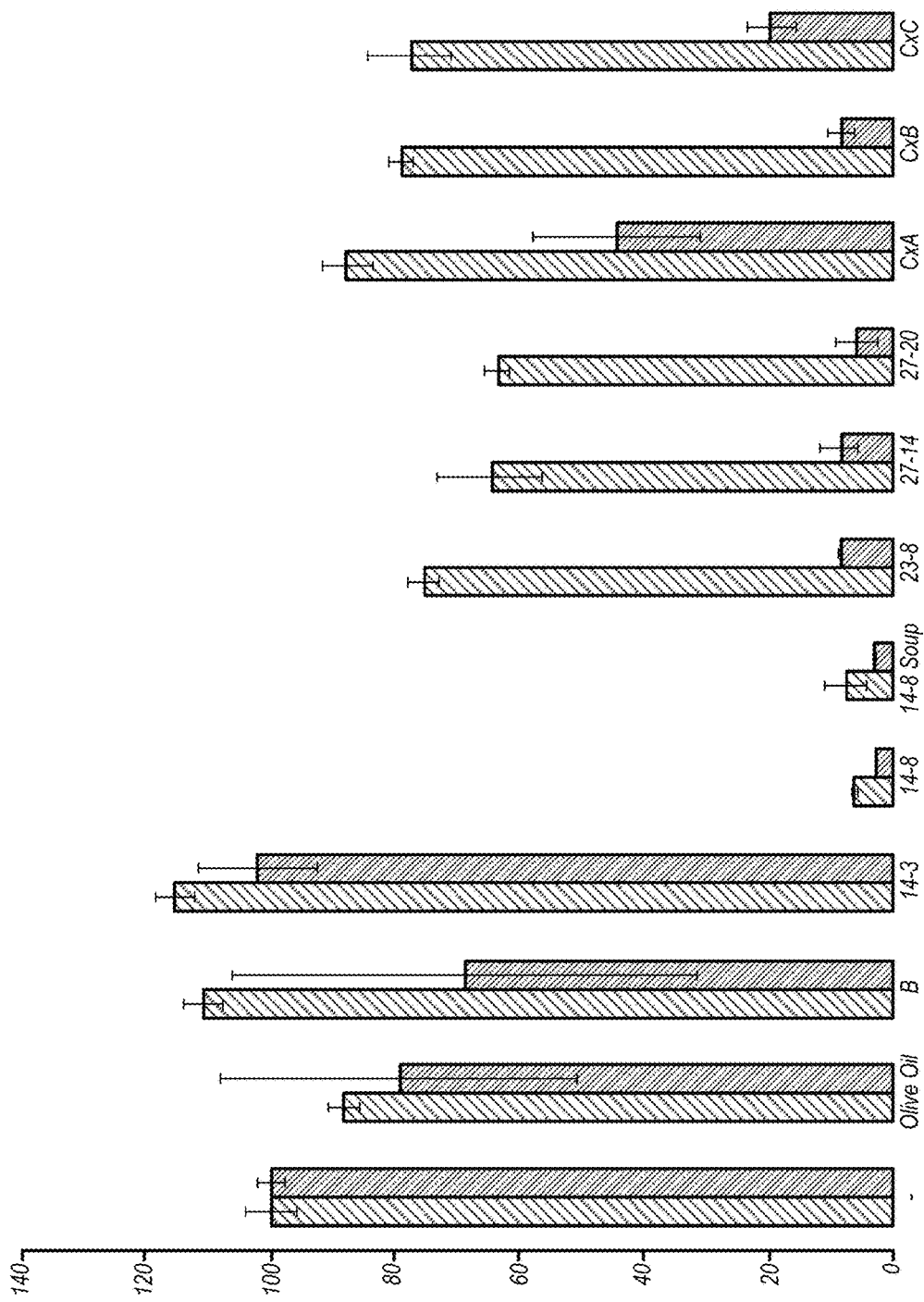
FIG. 12 depicts a graphical representation of a viability of a D-17 canine (osteosarcoma) cell line verses serval different compound and compositions at two different time intervals (24 and 72 hours).

FIG. 12 depicts a graphical representation of a viability of a D-17 canine (osteosarcoma) cell line verses serval different compound and compositions at two different time intervals. As is demonstrated in FIG. 12 lipofullerene-saccharide conjugate based compositions (e.g., 23-8) demonstrate an efficacy against a form of canine cancer.

Figure 13:
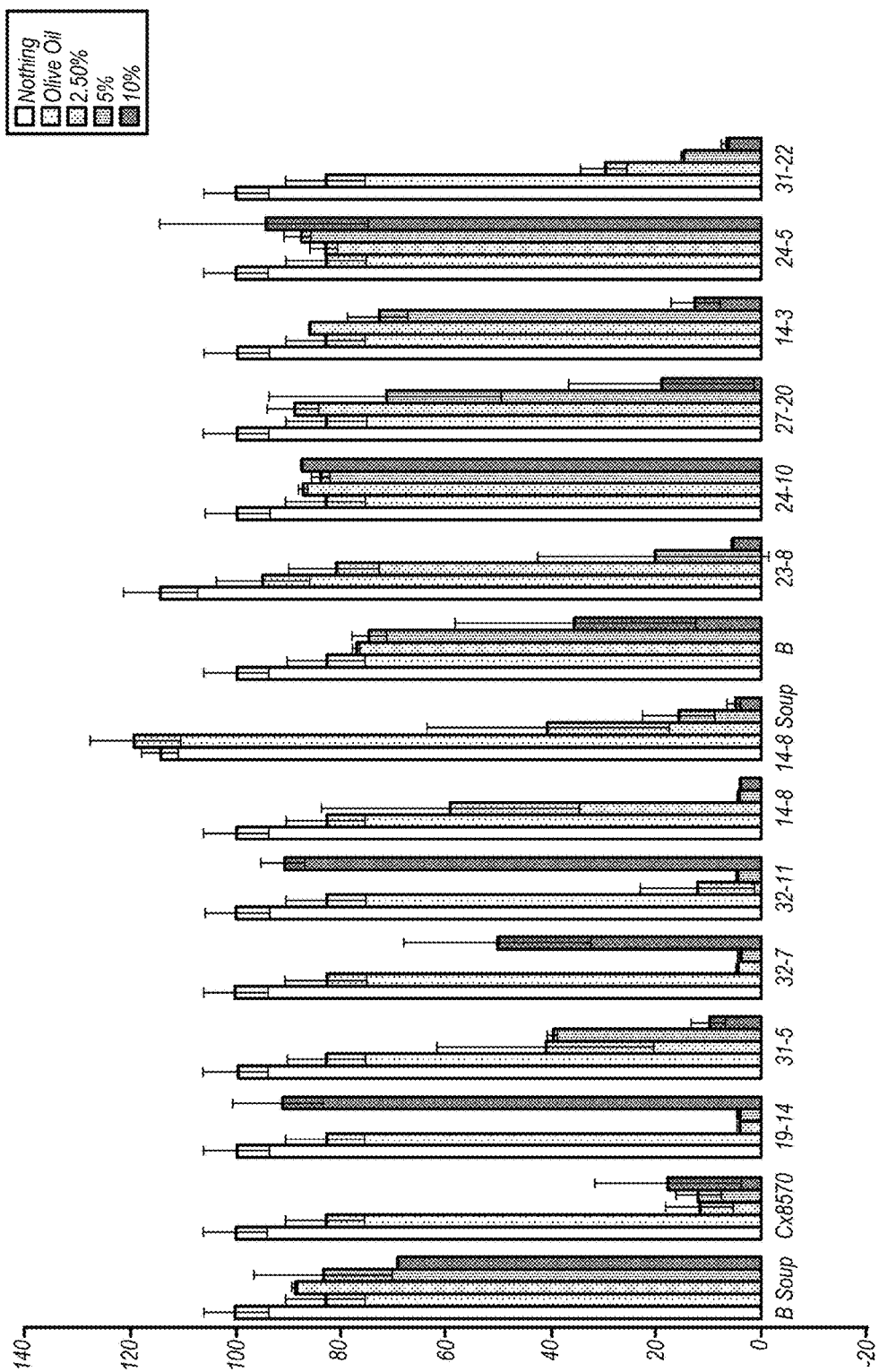
FIG. 13 depicts a graphical representation of a viability of a DD-1 canine (hemangiosarcoma) cell line verses serval different compound and compositions at a variety of different concentrations relative to untreated cell lines as well as solvent (e.g., olive oil).

FIG. 13 depicts a graphical representation of a viability of a DD-1 canine (hemangiosacoma) cell line verses serval different compound and compositions at a variety of different concentrations relative to untreated cell lines as well as solvent (e.g., olive oil). As is demonstrated in FIG. 13 lipofullerene-saccharide conjugate based compositions (e.g., 23-8) demonstrate an efficacy against a form of canine cancer.

Figure 14:
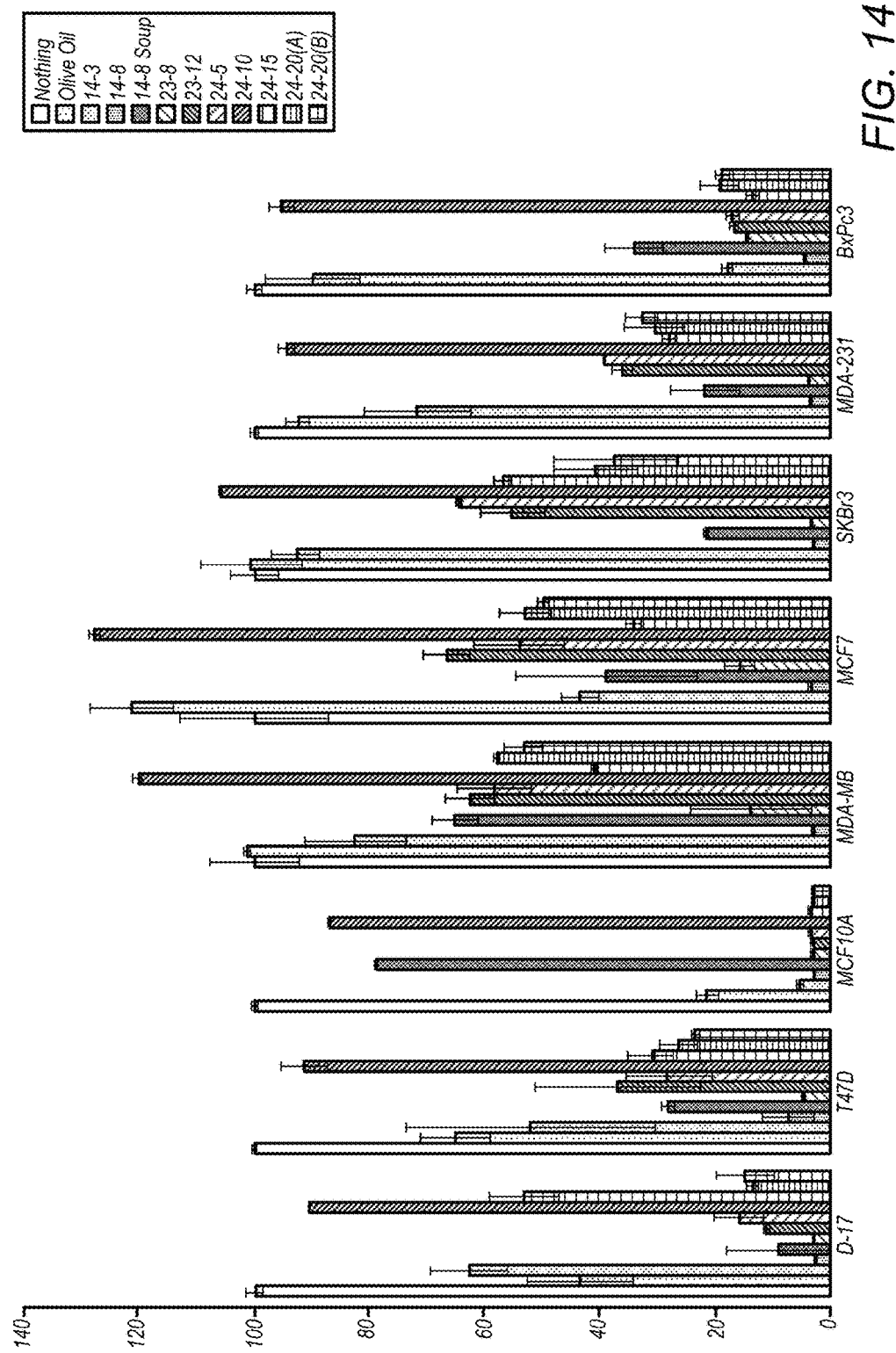
FIG. 14 depicts a graphical representation of a viability of a variety of different cancer cell line (i.e., D-17 canine (osteosarcoma) cell line, T-47D human breast (ductal carcinoma) cell line, MCF10A human breast (adenocarcinoma) cell line, MDA-MB human breast (adenocarcinoma) cell line, MCF7 human breast (adenocarcinoma) cell line, SK-Br3 human breast (adenocarcinoma) cell line, MDA-231 human breast (adenocarcinoma) cell line, and Bx-Pc3 human pancreatic (adenocarcinoma) cell line) verses serval different compound and compositions relative to untreated cell lines as well as solvent (e.g., olive oil).

FIG. 14 depicts a graphical representation of a viability of a variety of different cancer cell line (i.e., D-17 canine (osteosarcoma) cell line, T-47D human breast (ductal carcinoma) cell line, MCF10A human breast (adenocarcinoma) cell line, MDA-MB human breast (adenocarcinoma) cell line, MCF7 human breast (adenocarcinoma) cell line, SK-Br3 human breast (adenocarcinoma) cell line, MDA-231 human breast (adenocarcinoma) cell line, and Bx-Pc3 human pancreatic (adenocarcinoma) cell line) verses serval different compound and compositions relative to untreated cell lines as well as solvent (e.g., olive oil). As is demonstrated in FIG. 14 lipofullerene-saccharide conjugate based compositions (e.g., 23-8) demonstrate an efficacy against a number of known cancers.

Figure 15:
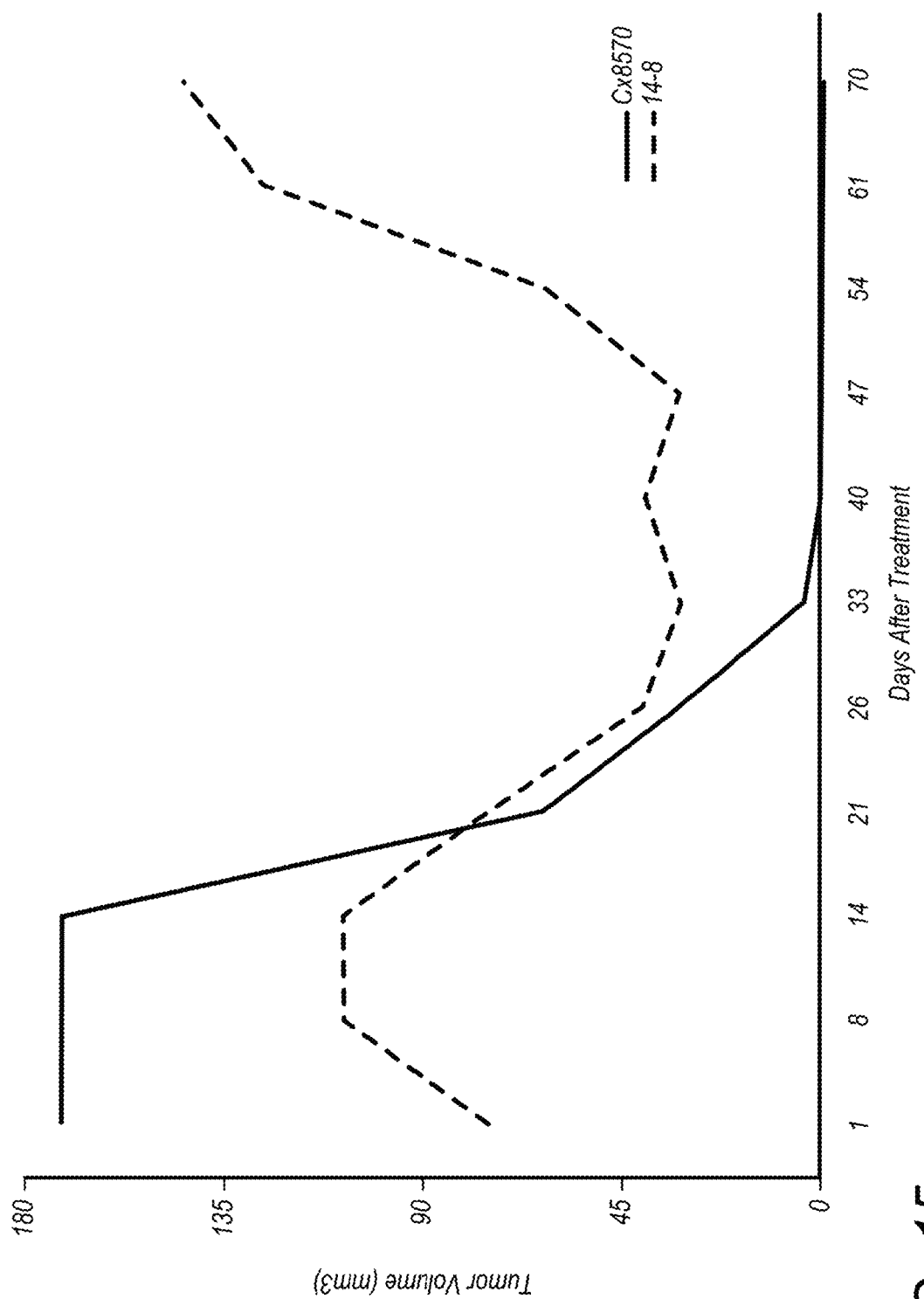
FIG. 15 depicts tumor volume over time after initiation of treatment with a C60 based composition 14-8 and a LC60S based composition Cx8570.

FIG. 15 depicts tumor volume over time after initiation of treatment with a C60 based composition 14-8 and a LC60S based composition Cx8570. As can be seen tumor volume does not increase with administration of the LC60S based composition Cx8570, while tumor volume does increase at least for a period of time upon administration of C60 based compositions. Thus you can see that Cx8570 eliminates the cells to a zero point while there is a resurgence of the cancer while using the 14-8.

Upon reviewing the results of the in vitro exposure of the various cancerous cell lines many of the C60 and LC60S based compositions have demonstrated an ability to mitigate the metastasis of a broad range of different types of cancers. In vitro experiments in some instances have demonstrated that C60 based compositions may inhibit metastasis of certain cancerous cell lines better than the LC60S based compositions. However, in vivo experiments detailed herein demonstrate that LC60S based compositions display a greater efficacy inhibiting the metastasis of cancers than C60 based compositions. This difference is theorized to be attributed to the saccharide coupled to the C60 allowing LC60S to penetrate deep within tumor masses in vivo (due to most cancers naturally absorbing saccharides for nutrients), while this benefit is not as obvious during in vitro tests as these tests typically involve small cell clusters at most. Saccharides are theorized to be used as a targeting mechanism for effectively transporting the C60 and Serrapeptase to and/or within a tumor. In order for metastasis to occur the mitochondria have to be downregulated and it needs to produce super oxides. Compositions described herein block the production of super oxides. Compositions described herein are stopping the replication of the cancer cells. Compositions described herein are blocking the inflammatory markers (e.g., IL-6 and IL-8) as well as is discussed in U.S. Pat. No. 9,308,243 to Mitchell et al. which is incorporated herein in its entirety.

Anecdotal Evidence

Case Study 1: An approximately 13.5 year old dog was diagnosed with cancer in April 2017 after a baseball sized tumor was removed from the dog's back leg. The cancer was diagnosed as Hemangiopericytoma Grade 3. Due to the dog's age and difficulty during and recovering from the tumor removal the vet did not believe that any of the standard treatment protocols would be effective in prolonging the subject's life. By November 2017 the subject's tumors had increased in size and the subject was having difficulty moving around and was generally lethargic and seemingly uncomfortable. In December 2017 the subject began a treatment protocol including the 23-8 composition described herein. Within a few weeks the subject displayed increased energy and stamina and as was still alive as of the end of January 2018 well beyond the expected lifespan based upon the original diagnosis.

Case Study 2: An approximately 10 year old dog was found to have a tumor between the subject's shoulder blades behind the subject's neck. A biopsy was not performed at the request of the owner due to the fact that the owner did not want to put the subject through the trauma of surgery or chemotherapy. It should be noted that a littermate of the subject died of cancer in March 2016. By the spring of 2017 the subject's tumor was approximately 20 cm×18 cm that was visible above the natural line of his back. The subject experience coughing, this was surmised to be due to the tumor pressing down on the subject's lungs. In April 2017 the subject began a treatment protocol including the 23-8 composition described herein in addition to a round of antimetastatic. By the end of January the coughing had stopped and the tumor was no longer obviously visible without touching the subject to feel the tumor (the owner estimated that the tumor had been reduced by ⅔ the tumors original size).

Case Study 3: A border collie mix dog was diagnosed with cancer on Jan. 11, 2018, at Oklahoma State University (OSU) Veterinary School. The subject was diagnosed with terminal cancer and was prescribed with chemo but this was only supposed to make the subject's final days more comfortable and nothing else. Within days the subject began a treatment protocol including the 23-8 composition described herein in addition to an immediate diet change to a ketogenic diet as well as stopping the administration of previously prescribed pain medication. Within 24 hours of the first dosage the subject regained previously lost appetite and within a few days the subject displayed increased energy and stamina and started regaining lost weight. The subject is currently behaving normally and showing no outward signs of sickness.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A chemical compound, comprising:
   a lipofullerene saccharide formed by reacting a lipid and a saccharide with a fullerene, wherein the lipofullerene saccharide comprises a general structural formula of [C60]x[C6H12O6]y[C18H34O2]z, wherein x is greater than or equal to 1, wherein y is greater than or equal to 1, wherein z is greater than or equal to 1, and wherein the saccharide comprises fructose.

2. The chemical compound of claim 1, wherein the fullerene comprises C60.

3. The chemical compound of claim 1, wherein the lipid comprises a fatty acid.

4. The chemical compound of claim 1, wherein the chemical compound is incorporated in a pharmaceutical composition, and wherein the pharmaceutical composition further comprises a physiologically acceptable carrier or diluent.

5. A method of inhibiting and/or ameliorating metastasis of neoplastic cells, comprising:
   administering to a subject an effective amount of a pharmaceutically acceptable formulation comprising a chemical compound comprising:
   a lipofullerene saccharide formed by coupling a lipid and a saccharide to a fullerene, wherein the lipofullerene saccharide comprises a general structural formula of [C60]x[C6H12O6]y[C18H34O2]z, wherein x is greater than or equal to 1, wherein y is greater than or equal to 1, wherein z is greater than or equal to 1, and wherein the saccharide comprises fructose; and
   inhibiting and/or ameliorating metastasis of neoplastic cells.

6. The method of claim 5, further comprising inhibiting and/or ameliorating a malady associated with neoplastic cells.

7. The method of claim 5, wherein the subject comprises a nonhuman mammal.

8. The method of claim 5, wherein the subject comprises an equine, canine, or feline.

9. The method of claim 5, wherein the subject comprises a human.

10. The method of claim 5, wherein the neoplastic cells are malignant.

11. The method of claim 5, wherein the neoplastic cells comprise pancreatic cancer cells.

12. The method of claim 5, wherein the neoplastic cells comprise prostate cancer cells.

13. The method of claim 5, wherein the neoplastic cells comprise lung cancer cells.

14. The method of claim 5, wherein the neoplastic cells comprise breast cancer cells.

15. The method of claim 5, wherein the neoplastic cells comprise colon cancer cells.

16. The method of claim 5, wherein the neoplastic cells comprise brain cancer cells.

* * * * *